(12) United States Patent
Piccariello et al.

(10) Patent No.: US 9,624,256 B2
(45) Date of Patent: Apr. 18, 2017

(54) COORDINATION COMPLEXES, PHARMACEUTICAL SOLUTIONS COMPRISING COORDINATION COMPLEXES, AND METHODS OF TREATING PATIENTS

(71) Applicant: SYNTHONICS, INC., Blacksburg, VA (US)

(72) Inventors: Thomas Piccariello, Blacksburg, VA (US); John D. Price, Blacksburg, VA (US); Robert A. Oberlender, Blacksburg, VA (US); Michaela E. Mulhare, Christiansburg, VA (US); Mary C. Spencer, Blacksburg, VA (US); Scott B. Palmer, Wilmette, IL (US)

(73) Assignee: SYNTHONICS, INC., Blacksburg, VA (US)

( * ) Notice: Subject to any disclaimer, the term of this patent is extended or adjusted under 35 U.S.C. 154(b) by 83 days.

(21) Appl. No.: 14/290,877

(22) Filed: May 29, 2014

(65) Prior Publication Data

US 2014/0274936 A1 Sep. 18, 2014

Related U.S. Application Data

(63) Continuation of application No. 12/788,073, filed on May 26, 2010, now Pat. No. 8,779,175, which is a continuation-in-part of application No. 11/824,411, filed on Jun. 29, 2007, now Pat. No. 7,799,937, which is a continuation-in-part of application No. 11/257,504, filed on Oct. 24, 2005, now abandoned.

(60) Provisional application No. 60/621,747, filed on Oct. 25, 2004.

(51) Int. Cl.
| | |
|---|---|
| *C07F 15/00* | (2006.01) |
| *A61K 31/28* | (2006.01) |
| *C07H 17/02* | (2006.01) |
| *A61K 31/165* | (2006.01) |
| *A61K 31/166* | (2006.01) |
| *A61K 31/295* | (2006.01) |
| *A61K 31/351* | (2006.01) |
| *A61K 31/4422* | (2006.01) |
| *A61K 31/7048* | (2006.01) |
| *A61K 45/06* | (2006.01) |
| *A61K 47/48* | (2006.01) |
| *C07F 3/00* | (2006.01) |
| *C07F 3/02* | (2006.01) |
| *C07F 3/06* | (2006.01) |
| *C07F 15/02* | (2006.01) |
| *C07F 15/04* | (2006.01) |

(52) U.S. Cl.
CPC ........... *C07H 17/02* (2013.01); *A61K 31/165* (2013.01); *A61K 31/166* (2013.01); *A61K 31/295* (2013.01); *A61K 31/351* (2013.01); *A61K 31/4422* (2013.01); *A61K 31/7048* (2013.01); *A61K 45/06* (2013.01); *A61K 47/481* (2013.01); *C07F 3/00* (2013.01); *C07F 3/003* (2013.01); *C07F 3/02* (2013.01); *C07F 3/06* (2013.01); *C07F 15/02* (2013.01); *C07F 15/04* (2013.01)

(58) Field of Classification Search
CPC ......... C07F 19/005; C07F 15/00; A61K 31/28
USPC ............................. 544/64; 514/492; 556/137
See application file for complete search history.

(56) References Cited

U.S. PATENT DOCUMENTS

| | | | |
|---|---|---|---|
| 4,035,360 | A | 7/1977 | Johnson et al. |
| 4,678,614 | A | 7/1987 | Kamienski et al. |
| 5,002,689 | A | 3/1991 | Mehta et al. |
| 5,043,168 | A | 8/1991 | Patel et al. |
| 5,073,630 | A | 12/1991 | Nunes et al. |
| 5,108,972 | A | 4/1992 | Wang et al. |
| 5,186,923 | A | 2/1993 | Piwnica-Worms et al. |
| RE34,222 | E | 4/1993 | Bloch |
| 5,277,897 | A | 1/1994 | Piwnica-Worms et al. |
| 5,324,637 | A | 6/1994 | Thompson et al. |
| 5,346,670 | A | 9/1994 | Renzoni et al. |
| 5,422,123 | A | 6/1995 | Conte et al. |

(Continued)

FOREIGN PATENT DOCUMENTS

| | | |
|---|---|---|
| EP | 0 188 351 A2 | 7/1986 |
| EP | 0 583 479 A1 | 2/1994 |

(Continued)

OTHER PUBLICATIONS

Morii et al., Clinical Pharmacology & Therapeutics, vol. 68, No. 6, pp. 613-616 (2000).*

(Continued)

*Primary Examiner* — Porfirio Nazario Gonzalez
(74) *Attorney, Agent, or Firm* — Ryan L. Marshall; Brinks Gilson & Lione

(57) ABSTRACT

A coordination complex having a physiologically acceptable $pK_a$ includes a metal and a biologically active agent. The $pK_a$ of the coordination complex is less than the $pK_a$ of the biologically active agent. A pharmaceutical solution for treating a patient includes a coordination complex and water, wherein the coordination complex is at least partially soluble in the water at physiological pH and in a therapeutically efficacious concentration. A method for treating a patient includes administering a pharmaceutical solution including a coordination complex and water to a patient in need of a biologically active agent.

21 Claims, 3 Drawing Sheets

(56) References Cited

U.S. PATENT DOCUMENTS

| | | |
|---|---|---|
| 5,422,125 A | 6/1995 | Skyler et al. |
| 5,494,682 A | 2/1996 | Cohen et al. |
| 5,494,793 A | 2/1996 | Schindele et al. |
| 5,538,959 A | 7/1996 | Mauskop |
| 5,582,839 A | 12/1996 | McCarty |
| 5,637,745 A | 6/1997 | Silverman et al. |
| 5,684,149 A | 11/1997 | Morrow |
| 5,776,498 A | 7/1998 | McCarty |
| 5,776,504 A | 7/1998 | McCarty |
| 5,786,392 A | 7/1998 | Silverman et al. |
| 5,849,337 A | 12/1998 | Dixon |
| 5,871,769 A | 2/1999 | Fleming et al. |
| 5,876,757 A | 3/1999 | McCarty |
| 5,972,868 A | 10/1999 | Athey et al. |
| 6,054,434 A | 4/2000 | Kropp et al. |
| 6,063,637 A | 5/2000 | Arnold et al. |
| 6,090,411 A | 7/2000 | Pillay et al. |
| 6,100,297 A | 8/2000 | Weglicki |
| 6,124,464 A | 9/2000 | Hogberg et al. |
| 6,129,924 A | 10/2000 | Maurel et al. |
| 6,132,420 A | 10/2000 | Dionne et al. |
| 6,245,357 B1 | 6/2001 | Edgren et al. |
| 6,248,368 B1 | 6/2001 | Valletta |
| 6,270,787 B1 | 8/2001 | Ayer |
| 6,283,953 B1 | 9/2001 | Ayer et al. |
| 6,287,295 B1 | 9/2001 | Chen et al. |
| 6,316,652 B1 | 11/2001 | Steliou |
| 6,333,050 B2 | 12/2001 | Wong et al. |
| 6,339,063 B1 | 1/2002 | Kropp et al. |
| 6,342,249 B1 | 1/2002 | Wong et al. |
| 6,368,626 B1 | 4/2002 | Bhatt et al. |
| 6,375,978 B1 | 4/2002 | Kleiner et al. |
| 6,376,549 B1 | 4/2002 | Fine et al. |
| 6,380,234 B1 | 4/2002 | Makino et al. |
| 6,403,616 B1 | 6/2002 | Erickson et al. |
| 6,413,952 B1 | 7/2002 | Luengo et al. |
| 6,417,196 B1 | 7/2002 | Daniel et al. |
| 6,498,247 B2 | 12/2002 | Evans et al. |
| 6,589,564 B2 | 7/2003 | Valletta |
| 7,041,650 B2 | 5/2006 | Abdel-Magid et al. |
| 7,195,778 B2 | 3/2007 | Fleshner-Barak et al. |
| 7,351,695 B2 | 4/2008 | Almarssoo et al. |
| 7,799,937 B2 | 9/2010 | Piccariello |
| 7,989,440 B2 | 8/2011 | Piccariello |
| 8,389,726 B2 | 3/2013 | Piccariello |
| 2002/0120165 A1 | 8/2002 | Zaworotko et al. |
| 2003/0224006 A1 | 12/2003 | Zaworotko et al. |
| 2006/0141054 A1 | 6/2006 | Piccariello |
| 2006/0264478 A1 | 11/2006 | Surmeier et al. |
| 2007/0026078 A1 | 2/2007 | Almarsson et al. |
| 2007/0059356 A1 | 3/2007 | Almarsson et al. |
| 2008/0015352 A1 | 1/2008 | Piccariello |
| 2009/0143338 A1 | 6/2009 | Piccariello |
| 2009/0197920 A1 | 8/2009 | Surmeier et al. |
| 2009/0209046 A1 | 8/2009 | Moulton et al. |
| 2009/0227446 A1 | 9/2009 | Chang et al. |
| 2009/0239946 A1 | 9/2009 | McKeown et al. |
| 2010/0209354 A1 | 8/2010 | Horcajada-Cortes et al. |
| 2010/0226991 A1 | 9/2010 | Horcajada-Cortes et al. |
| 2010/0273642 A1 | 10/2010 | Chang et al. |
| 2010/0311701 A1 | 12/2010 | Almarsson et al. |
| 2011/0052650 A1 | 3/2011 | Morris et al. |
| 2013/0059848 A1* | 3/2013 | Chen .................. C07D 487/04 514/234.2 |

FOREIGN PATENT DOCUMENTS

| | | |
|---|---|---|
| EP | 1 011 664 B1 | 11/2004 |
| EP | 1 510 214 A2 | 3/2005 |
| EP | 1 011 689 B1 | 1/2007 |
| JP | 09-227472 A2 | 9/1997 |
| WO | WO 93/19076 A1 | 9/1993 |
| WO | WO 03/013441 A2 | 2/2003 |
| WO | WO 03/051300 A2 | 6/2003 |
| WO | WO 03/066064 A2 | 8/2003 |
| WO | WO 03/074474 A2 | 9/2003 |
| WO | WO 2006/078925 A2 | 7/2006 |
| WO | WO 2007/050181 A2 | 5/2007 |
| WO | WO 2010/077655 A1 | 7/2010 |
| WO | WO 2011/149757 A1 | 12/2011 |

OTHER PUBLICATIONS

Kato et al., Journal of Clinical Pharmacology, vol. 42, pp. 1275-1280 (2002).*
Jones et al., Journal of American Chemical Society, vol. 128, No. 29, pp. 9378-9386 (published on the Web Jul. 4, 2006).*
Ridder et al., Analyical Chemistry, vol. 49, No. 13, pp. 20902098 (1977).*
Jain et al., Journal of Pharmaceutical and Biomedical Analysis, vol. 31, pp. 1035-1039 (2003).*
Lewis et al., Proceedings of the Society for Experimental Biology and Medicine, vol. 131, No. 4, pp. 1219-1222 (1969).*
Joseph Granot, Journal of the American Chemical Society, vol. 100, No. 9, pp. 2886-2891 (1978).*
Angels et al., Diseases of Nervous System, vol. 21, pp. 440-442 (1960).*
Chifotides et al., Journal of Inorganic Biochemistry, vol. 56, No. 4, pp. 249-264 (1994).*
Addison, C.C.; Sutton, D., "Ultraviolet Spectra of Anhydrous Metal Nitrates," *Journal of the Chemical Society (A)*, 1996, 1524-1528.
Afansas'ev, I.B.; Ostrakhovitch, E.A.; Mikhal'chik, E.V.; Ibragimova, G.A.; Korkina, L.G., "Enhancement of Antioxidant and Anti-Inflammatory Activities of Bioflavanoid Rutin by Complexation with Transition Metals," *Biochemical Pharmacology*, 2001, 61,677-684.
Agatonovic-Kustrin et al., "Spectrophotometric Determination of Furosemide and its Palladium (II) Complex," *Journal of Pharmaceutical & Biomedical Analysis*, 1990, 8, 983-986.
Ahrland, S., "Complex Formation in Protic and Aprotic Media," *Pure & Appl. Chem.* 1979, 51, 2019-2039.
Akers et al., "Alterations in Absorption of Dicumarol by Vaious Excipient Materials," *Journal of Pharmaceutical Sciences*, 1973, 62,391-395.
Almöf, J.; et al., "An Investigation of Correlation Effects in Transition-Metal Sandwich Complexes. Hartree-Fock Studies on a Series of Metallocenes," *Chemical Physics Letters*, 1984, 106, 266-269.
Almöf, J.; et al., "The Geometry and Bonding of Magnesocene an ab initio MO-LCAO Investigation," *Journal of Organometallic Chemistry*, 1983, 249, 303-313.
Alvarez-Núñez, F.A.; Yalkowsky, S.H., "Buffer Capacity and Precipitation Control of pH Solubilized Phenytoin Formulations," *Int. J. Pharm.*, 1999, 185, 45-49.
Ambre, M.D.; et al., "Effect of Co-administration of Aluminum and Magnesium Hydroxides on Absorption of Anticoagulants in Man," *Clinical Pharmacology and Therapeutics*, 1973, 14, 231-237.
Anderegg, G., "Correlation Between Thermodynamic Functions of Metal Complex Formation and Basicities of the Iminodiacetate Derivatives," 1991, 180, 69-72.
Bhattacharya, P.K., "Thermodynamic and Kinetic Properties of Metal Complexes," In *Metal Ions in Biochemistry*, Alpha Science International Ltd.,. Harrow, K., 2005, 16-65.
Bourgeois, B.F.D., "Pharmacokinetic Properties of Current Antiepileptic Drugs: What Improvements are Needed?" *Neurology*, 2000, 55 (Suppl. 3). S11-S16.
Baker, W.A.; Brown, P.M., "Metal Binding in Tetracyclines. Cobalt (II) and Nickel (II) Complexes," *Journal of the American Chemical Society*, 1966, 88, 1314-1317.
Barceló-Oliver et al., "Ternary Complexes Metal [Co(II), Ni(II), Cu(II) and Zn(II)]—ortho-iodohippurate (I-hip)-acyclovir. X-ray Characterization of Isostructural [(Co, Ni or Zn)(I-hip)$_2$(ACV)(H$_2$O)$_3$] with Stacking as a Recognition Factor," *Journal of Inorganic Biochemistry*, 2004, 98, 1703-1711.
Berezin, B.D. *Coordination Compounds of Porphyrins and Phthalocyanines*, John Wiley and Sons, New York, NY, 1981, 13-15, 107-108.

(56) References Cited

OTHER PUBLICATIONS

Berge, S.M. et al., "Review Article: Pharmaceutical Salts," *Journal of Pharmaceutical Sciences*, 1977, 66, 1-19.

Berners-Price, S.J.; Sadler, P.J., "Coordination Chemistry of Metallodrugs: Insights into Biological Speciation from NMR Spectroscopy," *Coordination Chemistry Reviews*, 1996, 151, 1-40 (abstract).

Bighley et al., "Chelates of Dicumarol I: Preparation and Structure Identification of Magnesium Chelate," *Journal of Pharmaceutical Sciences*, 1977, 66, 1124-1127.

Binder et al., *Gastroenterology*, 1998, 115, 1295-1301.

Bontchev et al., "Copper(II) Complexes of Blood Pressure Active Drugs," *Transition Metal Chemistry*, 2002, 27, 1-21.

Briganti, F.; Tilli, S.; Mincione, G.; Mincione, F.; Menabuoni, L.; and Supuran, C.T., "Carbonic Anhydrase Inhibitors. Metal Complexes of 5-(2-Chlorophenyl)-1,3,4-thiadiazole-2-sulfonamide with Topical Intraocular Pressure Lowering Properties: The Influence of Metal Ions Upon the Pharmacological Activity," *Journal of Enzyme Inhibition*, 2000, 15, 185-200.

Buschmann, H.J.; Schollmeyer, E., "Complexation of Alkaline Earth (Group 2A) Cations by Noncyclic, Macrocyclic and Macrobicyclic Ligands in Propylene Carbonate Solutions," *Thermochimica Acta*, 1992, 211, 13-20 (abstract).

Cai, Y.Y.; Yap, C.W.; Wang, Z.; Ho, P.C.; Chan, S.Y.; Ng, K.Y.; Ge, Z.G.; Lin, H.S., "Solubilization of Vorinostat by Cyclodextrins," *J. Clin. Pharm. and Therapeutics*, 2009, 34, 1-6.

Chakrawarti, P.B.; Vijayvargiya, S., "Study of Metal Complexes of Ampicillin," *Proceedings of the National Academy of Sciences, India, Section A: Physical Sciences*, 1991, 61, 277-284 (abstract).

ChemSilico, "CSLogWS . . . Introduction to Solubility"; 2003; available on the internet at http://www.chemsilico.com/CS_prWS/WSintro.html as of May 24, 2010; 4 pgs.

Chisolm, M.H.; Gallucci, J.; Phomphrai, K., "Coordination Chemistry and Reactivity of Monomeric Alkoxides and Amides of Magnesium and Zinc Supported by the Diiminato Ligand $Ch(CMeNC_6H_3-2,6-^iPr_2)_2$. A Comparative Study," *Inorganic Chemistry*, 2002, 41, 2785-2794.

Chohan et al., "Antibacterial and Antifugal Mono-and Di-substituted Symmetrical and Unsymmetrical Triazine-derived Schiff-bases and their Transition Metal Complexes," *Journal of Enzyme Inhibition and Medicinal Chemistry*, 2004, 19, 161-168.

Chohan et al., "Binding of Transition Metal Ions [Cobalt, Copper, Nickel and Zinc] with Furanyl-, Thiophenyl-, Pyrrolyl-, Salicylyl- and Pryidyl-Derived Cephalexins as Potent Antibacterial Agents," *Journal of Enzyme Inhibition and Medicinal Chemistry*, 2004, 19, 51-56.

Chohan et al., "Isatin-derived Antibacterial and Antifungal Compounds and their Transition Metal Complexes," *Journal of Enzyme Inhibition and Medicinal Chemistry*, 2004, 19, 417-423.

Choi, J.W.; Kim, W.K., "Is Topiramate a Potential Therapeutic Agent for Cerebral Hypoxicilschemic Injury" *Exp. Neurol.*, 2007, 203, 5-7.

Cloyd, J.C., "Pharmacokinetics and Safety of Intravenous Topiramate in Adult Patients"; 2010; available on the internet at http://www.clinicaltrials.gov/ct2/show/NCT00233012?term=topiramate&rank=16 as of Mar. 20, 2010; 3 pgs.

Codd, et al., "Traversing the Coordination Chemistry and Chemical Biology of Hydroxamic Acids," *Coordination Chemistry Reviews, Elsevier Science*, Amsterdam, NL, 252(12-14):1387-1408, Jul. 2008.

Cook, D.H.; Fenton, D.E.; Drew, M.G.; McFall, S.G.; Nelson, S.M., "Seven-Coordination in Metal Complexes of Quinquedentate Macrocyclic Ligands. Part 6. Magnesium Complexes of Macrocyclic Ligands Containing Nitrogen and Oxygen Donor Atoms," *Journal of the Chemical Society, Dalton Transactions: Inorganic Chemistry*, 1977, 5, 446-449. (abstract).

Cotton, F.A.; Francis, R., "Sulfoxides as Ligands. I. A Preliminary Survey of Methyl Sulfoxide Complexes," *Journal of the American Chemical Society*, 1960, 82, 2986-2991.

Cowan, J.A. editor. *The Biological Chemistry of Magnesium*, VCH Publishers, Inc. New York, NY, 1995, 1-21, 85-108 and 111-117.

Crowder, M.W. et al., "Characterization of the Metal-Binding Sites of the Beta-Lactamase from Bacteroides Fragilis," *Biochemistry*, 1996, 35, 12126-12132.

Dabrowiak, J.C. *Metals in Medicine*, John Wiley & sons, Ltd., New York, NY, 2009, 55.

Davis, S., "The Copper Complexes of Mono and Diiodotyrosine, Thyronine, Di- and Triiodothyronine, and Thyroxine," *J. Biol. Chem.*, 1957, 224, 759-766.

De Jong, J.C. et al., "The Structural Unit of the Thiazide-Sensitive NaCl Cotransporter is a Homodimer," *J. Biol. Chem.*, 2003, 278, 24302-24307.

Doyle, L.W.; Crowther, C.A.; Middleton, P.; Marret, S.; Rouse, D., "Magnesium Sulphate for Women at Risk of Preterm Birth for Neuroprotection of the Fetus," *Cochrane Database of Systematic Reviews*, 2009, Issue 1, Art. No., CD004661, 93 pgs (Including title page and table of contents).

du Plessis, A.J., Cerebrovascular Injury in Premature Infants: Current Understanding and Challenges for Future Prevention,: *Clin. Perinatol.*, 2008, 35, 609-641.

Emara et al., *Analytica Chimica Acta*, vol. 489, No. 1, pp. 115-123 (2003).

Evans, D.A. et al., "Diasteroselective Magnesium Halide-Catalyzed anti-Aldol Reactions of Chiral N-Acyloxazolidinones," *J. Am. Chem. Soc.*, 2002, 124, 392-393.

Evans, I.P.; Spencer, A.; Wilkinson, G., "Dishlorotetrakis (dimethylsulphoxide) ruthenium(II) and its Use as a Source for Some New Ruthenium(II) Complexes," *Journal of the Chemical Society, Dalton Transactions*, 1973, 204-209.

Faegri, K. et al., "Molecular Structures of Alkaline-Earth-Metal Metallocenes: Electron Diffraction and ab Initio Investigations," *Organometallics*, 1990, 9, 372-379.

Flammengo, R.; Wojciechowski, K.; Crego-Calama, M.; Timmerman, P.; Figoli, A.; Wessling, M.; Reinhoudt, D.N., "Heme-Protein Active Site Modules via Self-Assembly in Water," *Organic Letters*, 2003, 5, 3367-3370.

Frew, A.J.; Johnstone, R.W.; Bolden, J.E., "Enhancing the Apoptotic and Therapeutic Effects of HDAC Inhibitors," *Cancer Lett.*, 2009, 280, 125-133.

Frijlink, H.W.; Visser, J.; Hefting, N.R.; Oosting, R.; Meijer, D.K.F.; Lerk, C.F., "The Pharmacokinetics of β-Cyclodextrin and Hydroxypropyl-β-Cyclodextrin in the Rat," *Pharm. Res.*, 1990, 7, 1248-1252.

Fujii, T., "Alkali-Metal Ion/Molecule Association Reactions and Their Applications to Mass Spectrometry," *Mass Spectrometry Reviews*, 2000, 19, 111-138.

Futaki, S.; Miwa, M.; Nakase, I.; Tadokoro, A.; Zhang, Y.; Nagaoka, M.; Wakako, N.; Sugira, Y., "Arginine Carrier Peptide Bearing Ni(II) Chelator to Promote Cellular Uptake of Hisitidine-Tagged Proteins," *Bioconjugte Chemistry*, 2004, 15, 475-481.

Galinkin, J.L.; Kurth, C.D.; SDhi, H.; Priestley, M.A.; Loepke, A.W.; Adamson, P.C., "The Plasma Pharmacokinetics and Cerebral Spinal Fluid Penetration of Intravenous Topiramate in Newborn Pigs," *Biopharm. Drug Dispos.*, 2004, 25, 265-271.

Galvan-Tejada et al., *Journal of Inorganic Biochemistry*, vol. 91, pp. 339-348 (2002).

Gantt, Stephanie L. et al., "Catalytic activity and inhibition of human histone deacetylase 8 is dependent on the identity of the active site metal ion," *Biochemistry, American Chemical Society*, 45(19):6170-6178 (May 2006).

Gerard, C. Chehhal, H., "Stability of Metal Complexes with Ligands of Biological Interest: Dopamine and Adrenaline," *Bulletin de la Societe Chimique de France*, 1997, 134, 1069-1074 (abstract).

Golcu et al., "Synthesis of Binuclear Copper (II) Complex of the Antihypertensive Drug Pindolol," *KSU Journal of Science and Engineering*, 2005, 8, 4-9.

Golcu et al., "Synthesis and Characterization of Metal Complexes of Acebutolol, Atenolol, and Propanolol Antihypertension Drugs," *Synthesis and Reactivity in Inorganic and Metal-Organic Chemistry*, 2004, 34, 1259-1275.

(56) References Cited

OTHER PUBLICATIONS

Goodin, S., "Oral Chemotherapeutic Agents: Understanding Mechanisms of Action and Drug Interactions," *Am. J. Health Syst. Pharm.*, 2007, 64, Suppl. 5, S15-S24.

Griffith, D. et al., "A Novel Anti-Cancer Bifunctional Platinum Drug Candidate with dual DNA Binding and Histone Deacetylase Inhibitory Activity," *Chemical Communications—Chemcom, Royal Society of Chemistry*, 28(44):6735-6737 (Nov. 2009).

Grundy, J.; Coles, M.P.; Hitchcock, P.B., "A New Class of Linked-bis (N,N'-dialkylamidinate) Ligand: Applications in the Synthesis of Bimetallic Aluminum Complexes," *Journal of Organometallic Chemistry*, 2002, 662, 178-187 (abstract).

Hockly, E.; Ricon, V.M.; Woodman, B.; Smith, D.L.; Zhou, X.; Rosa, E.; Sathasivam, K.; Ghazi-Noori, S.; Mahal, A.; Lowden, P.A.S.; Steffan, J.S.; Marsh, J.L.; Thompson, L.M.; Lewis, C.M.; Marks, P.A.; Bates, G.P., "Suberoylanilide Hydroxamic Acid, A Histone Deacetylase Inhibitor, Ameliorates Motor Deficits in a Mouse Model of Huntington's Disease," *Proc. Natl. Acad. Sci.*, 2003, 100, 2041-2046.

Hartmann et al., "Functional Zinc Complexes of Tris(midazolymethyl)amine Ligands," *Chem. Ber.*, 1994, 127, 2123-2127 (English abstract).

Hartmann et al., "Zinc Complexes of Sulfonamides," *Journal of Chemical Sciences*, 1994, 49, 1725-1730 (English abstract).

Herbst, W. et al.; *Industrial Organic Pigments*, VCH Publishers, Inc., New York, NY, 1993, 21, 392.

Hondrellis, V. et al., "Metal Complexes of the Diuretic Drug Furosemide," *Monatshefte für Chemie*, 1988, 119, 1091-1101.

Ichiyanagi, T. et al., "Enantioselective Diels-Alder Reaction Using Chiral Mg Complexes Derived from Chiral 2-[2[Alkyl- or 2-[2-[(Arylsulfonyl)amino]phenyl]-4-phenyl-1,3-oxazoline," *Journal of Organic Chemistry*, 1997, 62, 7937-7941.

Ikeda, Y. et al., "Furosemide-Sensitive Calcium Rise Induced by GABAA-Receptor Stimulation in Cultures of Embryonic Rat Striatal Neurons," *Jpn. J. Pharmacol.*, 1997, 74, 165-169.

Jones, C.E.; Taylor, P.J.; McEwan, A.G.; Hanson, G.R., "Spectroscopic Characterization of Copper(II) Binding to the Immunosuppressive Drug Mycophenolic Acid," *J. Am. Chem. Soc.*, 2006, 128, 9378-9386.

Jordan, B.A. et al., "G-protein-coupled Receptor Heterodimerization Modulates Receptor Function," *Nature*, 1999, 399, 697-700.

Kawai et al., Chem. Pharm. Bull., vol. 44, No. 8, pp. 1425-1430 (1996).

Kelly, W.K.; Marks, P.A., "Drug Insight: Histone Deacetylase Inhibitors—Development of the New Targeted Anticancer Agent Suberoylanilide Hydroxamic Acid," *Nature Clinical Practice: Oncology*, 2005, 2,150-157.

Kelly, W.K.; Richon, V.M.; O'Connor, O.; Curley, T.; MacGregor-Curtelli, B.; Tong, W.; Kiang, M.; Schwartz, L.; Richardson, S.; Rosa, E.; Drobnjak, M.; Cordon-Cordo, C.; Chiao, J.H.; Rifkind, R.; Marks, P.A.; Scher, H., "Phase I Clinical Trial of Histone Deacetylase Inhibitor: Suberoylanilide Hydroxamic Acid Administered Intravenously," *Clin. Cancer Res.*, 2003, 9, 3578-3588.

Kiraly, R.; Martin, R.B., "Metal Ion Binding to Daunorubicin and Quinizarin," *Inorganica Chimica Acta*, 1982, 67, 13-18.

Kovala-Demertzi, D.; Metzafos, D.; Terzis, A., "Metal Complexes of the Anti-Inflammatory Drug Sodium [2-[(2,6-Dichlorophenyl)amino[phenyl]acetate (Diclofenac Sodium). Molecular and Crystal Structure of Cadmium Diclofenac," *Polyhedron*, 1993, 12, 1361-1370.

Lach et al., "Diffuse Reflectance Studies of Solid-Solid Interactions," *Journal of Pharmaceutical Sciences*, 1970, 59, 1261-1264.

Larner, J. et al., "Isolation, Structure, Synthesis, and Bioactivity of a Novel Putative Insulin Mediator. A Galactosamine chiro-Inositol Psuedo-Disaccharide $Mn^{2+}$Chelate with Insulin-like Activity," *J. Med. Chem.*, 2003, 46, 3283-3291.

Lambs, L.; Berthon, G., "Metal Ion-Tetracycline Interactions in Biological Fluids. Part 7. Quantitative Investigation of Methacycline Complexes with Ca(II), Mg(II), Cu(II) and Zn(II) Ions and Assessment of their Biological Significance," *Inorganica Chimica Acta*, 1988, 151, 33-43.

Lee, Y.C.; Zocharski, P.D.; Samas, B., "An Intravenous Formulation Decision Tree for Discovery Compound Formulation Development," *Int. J. Pharm.*, 2003, 253, 111-119.

Lippert, B., "Ligand-$pK_a$ Shifts Through Metals: Potential Relevance to Ribozyme Chemistry," *Chemistry & Biodiversity*, 2008, 5, 1455-1474.

Lonardi, S.; Bortolami, A.; Stefani, M.; Monfardini, S., "Oral Anticancer Drugs in the Elderly: An Overview," *Drugs Aging*, 2007, 24, 395-410.

Lutz, M. Müller, G., "Authentication of Aminomethyl(hydrogen)phosphonate Coordination to a Main Group Metal: Synthesis and Crystal Structure of $[Mg(O_3PCH_2NH_3)_2(H_2O_2] 2H_2O$," *Inorganica Chimica Acta*, 1995, 232, 189-193.

Ma, Z.; Han, S.; Kravtsov, V.C.; Moulton, B., "Confirmational Isomerism and Hydrogen-Bonded Motifs of Anion Assisted Supramolecular Self-Assemblies Using $Cu^{II}/Co^{II}$ salts and Pyridine=4-Acetamide," *Inorganica Chimica Acta*, 2010, 363, 387-394.

Ma, Z.; Hopson, R.; Cai, C.; Han, S.; Moulton, B., "Modifying Lipophilicitirs of Zn(II) Coordination Species by Introduction of Ancillary Ligands: A Supramolecular Chemistry Approach," *Crystal Growth & Design*, 2010, 10, 2376-2381.

Ma, Z.; Moulton, B., "Mixed-Ligand Coordination Species: A Promising Approach for 'Second-Generation' Drug Development," *Crystal Growth & Design*, 2007, 7, 196-198.

Ma, Z.; Moulton, B., "Recent Advances of Discrete Coordination Complexes and Coordination Polymers in Drug Delivery," *Coordination Chemistry Reviews*, 2011, Article in Press, 19 pgs.

Ma, Z.; Moulton, B., "Supramolecular Medicinal Chemistry: Mixed-Ligand Coordination Complexes," *Molecular Pharmaceutics*, 2007, 4, 373-385.

Mahto, C.B., et al., "Chelates of .beta.-[3,5-diiodo-4-(3,5-diiodo-4-hydroxyphenoxy)phenyl]- .alpha.-aminopropionic acid with some divalent metal ions," 16(3)*Acta Cientia Indica* 311-316 (1990).

Manfredini, S.; Pavan, B.; Vertuani, S.; Scaglianti, M.; Compagnone, D.; Biondi, C.; Scaturrin, A.; Tanganelli, S.; Ferraro, L.; Prasad, P.; Dalpiaz, A., "Design, Synthesis and Activity of AscorbicAcid Prodrugs of Nipecotic, Kynurenic and Diclophenamic Acids, Liable to Increase Neurotropic Activity," *J. Med. Chem.*, 2002, 45, 559-562.

Marks, P.A.; Breslow, R. "Dimethyl Sulfoxide to Vorinostat: Development of this Histone Deacetylase Inhibitor as an Anticancer Drug," *Nat. Biotechnol.*, 2007, 25,84-90.

Martell, A.E. et al. *Chemistry of the Metal Chelate Compounds*, Prentice-Hall, Inc. Englewood Cliffs, NJ, 1962, 181-237.

Martell, et al., "Factors Affecting Stabilities of chelate, Macrocyclic and Macrobicyclic Complexes in Solution," *Coordination Chemistry Reviews*, 1994, 133, 39-65.

McCallister, J.D.; Chin, T.F.; Lach, J.L., "Diffuse Reflectance Studies of Solid-Solid Interactions IV: Interaction of Bishydroxycoumarin, Furosemide, and Other Medicinal Agents with Various Adjuvants," *J. Phar. Sci.*, 1970, 59, 1286-1289.

Miller, S.; Heurtaux, D.; Baati, T.; Horcajada, P.; Greneche, J.M.; Serre, C., "Biodegradable Therapeutic MOFs for the Delivery of Bioactive Molecules," Chem. Commun., 2010, 46, 4526-4528.

Ming, L.J., "Structure and Function of 'Metalloantibiotics'," *Medical Research Review*, 2003, 23, 697-762.

Minucci, S.; Pelicci, P.G. "Histone Deacetylase Inhibitors and the Promise of Epigenetic (and more) Treatments for Cancer," Nature Reviews: Cancer, 2006, 6, 38-51.

Miyamoto, T. et al., "High Affinity and Specificity of Dimeric Binding of Thyroid Hormone Receptors to DNA and Their Ligand-Dependent Dissociation," *Molecular Endocrinology*, 1993, 7, 224-231.

Mizuguchi, J., "Interactions of Magnesium Phthalocyanine as Evaluated by Energy Partition Analysis," *J. Phys. Chem. A*, 2001, 105, 10719-10722.

(56) References Cited

OTHER PUBLICATIONS

Mizuguchi, J. et al., "Interpretation of the Near-Infrared Absorption of Magnesium Phthalocyanine Complexes in Terms of Exciton Coupling Effects," *J. Phys. Chem. A*, 1999, 103, 8193-8199.

Mojumdar, S.C.; Melnik, M.; Jona, E., "Thermal Decomposition and IR Spectra of Mg(II) Compounds with Caffeine," *Chemical Papers*, 1999, 53, 309-314 (abstract).

Moulton, B.; Zaworotko, M.J., "From Molecules to Crystal Engineering: Supramolecular Isomerism and Polmorphism in Network Solids," *Chem. Rev.*, 2001, 101, 1629-1658.

Moustafa, Azza A.M., Journal of Pharmaceutical and Biomedical Analysis, vol. 22, No. 1, pp. 45-58 (2000).

Muller, J.G.; Burrows, C.J., "Metallodrug Complexes that Mediate DNA and Lipid Damage Via Sulfite Autoxidation: Coper (II) Famotidine and Iron (III) Bis(Salicylglycine)," *Inorganica Chimica Acta*, 1998, 275-276, 314-319.

Murakami, Y. et al., "Stability Order in Metal Chelate Compounds. II. 5-(p-Sulfophenylazo)-Salicylate Complexes," *Bulletin of the Chemical Society of Japan*, 1964, 37, 268-272.

Nijenhuis, T. et al., "Thiazide-Induced Hypocalciuria is Accompained by a Decreased Expression of $Ca^{2+}$ Transport Protiens in Kidney," Kidney International, 2003, 64, 55-564.

Nolan, K.B.; Soudi, A.A. "Synthesis and Characterization of Copper(II), Zinc(II) and Cobalt(II) Complexes of Salicylglycine, a Metabolite of Aspirin," *Inorganica Chimica Acta*, 1995, 230, 209-210.

O'Connor, O.A.; Heaney, M.L.; Schwartz, L.; Richardson, S.; WIllim, R.; MacGregor-Cortelli, B.; Curly, T.; Moskowitz, C.; Portlock, C.; Horwitz, S.; Zelenetz, A.D.; Frankel, S.; Richon, V.; Marks, P.; Kelly, W.K., "Clinical Experience with Intravenous and Oral Formulations of the Novel Histone Deacetylase Inhibitor Suberoylanilide Hydroxamic Acid in Patients with Advanced Hematologic Malignancies," *J. Clin. Oncol.*, 2006, 24, 166-173.

Ohyama, T.; Cowan, J.A., "Calorimetric Studies of Metal Binding to Tetracycline. Role of Solvent Structure in Defining the Selectivity of Metal Ion-Drug Interactions," *Inorganic Chemistry*, 1995, 34, 3083-3086.

Orita, Y. et al. "A Metal Complexing Property of Furosemide and Bumetanide: Determination of pK and Stability Constant," *Arzneim.-Forsch. (Drug Res.)*, 1976, 26, 11-13.

Paluchowska, B.; Maurin, J.K.; Leciejewicz, J., "Direct and Outer-Sphere Coordination of the Magnesium Ions in the Crystal Structures of Complexes with 2-Furancarboxylic Acid (I) and 3-Furancarboxylic Acid (II)," *Journal of Chemical Crystallography* 1997, 27, 177-182 (abstract).

Park, G.; Tomlinson, J.T.; Melvin, M.S.; Wright, M.W.; Day, C.S.; Manderville, R.A., "Zinc and Copper Complexes of Prodigiosin: Implications for Copper Medicated Double-Strand DNA Cleavage," *Organic Letters*, 2003, 5, 113-116.

Parrill, A.L. et al., "HIV Integrase Inhibitor Interactions with Active-Site Metal Ions: Fact or Fiction?," in *Computational Organometallic Chemistry*, ed. Cundari, T.R.; Marcel Dekker, Inc., New York, NY, 2001, 189-196.

Pastor, A.; Martinez-Viviente, E., "NMR Spectroscopy in Coordination Supramolecular Chemistry: A Unique and Powerful Methodology," *Coordination Chemistry Reviews*, 2008, 252, 2314-2345.

Patel et al., *Pharmaceutical Chemistry Journal*, vol. 42, No. 12, pp. 687-692 (2008).

Pecoraro, V.L. et al., "Stability Constants of $Mg^{2+}$ and $Cd^{2+}$ Complexes of Adenine Nucleotides and Thionucleotides and Rate Constants for Formation of Dissociation of Mg ATP and Mg ADP," Biochemistry, 1984, 23, 5262-5271.

Pierloot, K., "Nondynamic Correlation Effects in Transition Metal Coordination Compounds," in *Computational Organometallic Chemistry*, ed. Cundari, T.R.; Marcel Dekker, Inc., New York, NY, 2001, 123-158.

Quamme, G.A., "Effect of Furosemide on Calcium and Magnesium Transport in the Rat Nephron," *American Journal of Physiology*, 1981, 241, F340-F347.

Rajan et al., "Metal Chleates of L-DOPA for Improved Replenishment of Dopaminergic Pools," *Brain Research*, 1976, 107, 317-331.

Robinson, G.H. et al., "Unusual Trimetallic Magnesium Cations and Adamantyl Anions of Aluminum and Gallium," *Journal of Organometallic Chemistry*, 2003, 666, 7-13.

Rubin, E.H.; Agrawal, N.G.B.; Friedman, E.J.; Scott, P.; Mazina, K.E.; Sun, L.; Du, L.; Ricker, J.L.; Frankel, S.R.; Gottesdiener, K.M.; Wagner, J.A.; Iwamoto, M., "A Study to Determine the Effects of Food and Multiple Dosing on the Pharmacokinetics of Vorinostat Given Orally to patients with Advanced Cancer," *Clin. Cancer Res.*, 2006, 12, 7039-7045.

Schwendeman, S.P. et al., "Comparison of the Effects of $Mg(OH)_2$ and Sucrose on the Stability of Bovine Serum Albumin Encapsulated in Injectable Poly(D,L-lactide-co-glycolie) Implants," *Biomaterials*, 2002, 23, 239-245.

Schwietert, C.W.; McCue, J.P. "Coordination Compounds in Medicinal Chemistry," *Coordination Chemistry Reviews*, 1999, 184, 67-89.

Sham, S.; Wu, G., "Solid-State 25 Mg Study of Inner-Sphere $Mg^{2+}$ Binding Complexes," *Inorganic Chemistry*, 2000, 39, 4-5 (abstract).

Shank, R.P.; Gardocki, J.F.; Streeter, A.J.; Maryanoff, B.E., "An Overview of the Preclinical Aspects of Topiramate: Pharmacology, Pharmacokinetics, and Mechanism of Action," *Epilepsia*, 2000, 41 (Suppl.1), S3-S9.

Sharma, U.N., et al., "Chelates of .beta.-[3,5-diiodo-4-(3',5'-diiodo-4'- hydroxyphenoxy)phenyl]- .alpha.-aminopropionic acid with some divalent metal ions," 26(2) *Acta Cientia Indica* 33-36 (2000).

Siegel, D.; Hussein, M.; Belani, C.; Robert, F.; Falanis, E.; Richon, V.M.; Garcia-Vargas, J.; Sanz-Rodriguez, C.; Rizvi, S., "Vorinostat in Solid and Hematologice Malignancies," *J. Hematol. Oncol.*, 2009, 2, 31, (11 pgs).

Skorey, K. et al., "How Does Alendronate Inhibit Protein-Tyrosine Phosphatases?" *J. Biol. Chem.*, 1997, 272, 22472-22480.

Song et al., Helvetica Chimica Acta, vol. 77, pp. 1738-1756 (1994).

Stella, V.J.; He, Q., "Cyclodextrins," *Toxicol. Pathol.*, 2008, 36, 30-42.

Sultana, Najma, et al., "Synthesis, spectroscopic, and biological evaluation of some levofloxacin metal complexes," 22(3) *Medicinal Chemistry Journal* 1371-1377 (Mar. 2013), published online Jun. 16, 2012.

Supuran, C.T.; Scozzafava, A.; Mincione, F.; Menabuoni, L.; Briganti, F.; Mincione, G.; Jitianu, M., "Carbonic Anhydrase Inhibitors. Part 60. The Topical Intraocular Pressure-Lowering Properties of Metal Complexes of a Heterocyclic Sulfonamide: Influence of the Metal Ion Upon Biological Activity," *European Journal of Medicinal Chemistry*, 1999, 34, 585-595.

Supuran, C.T.; Scozzafava, A.; Saramet, I.; Banciu, M.D., "Carbonic Anhydrase Inhibitors. Inhibition of Isozymes, I, II, and IV with Heterocyclic Mercaptans, Sulfenamides, Sulfonamises and their Metal Complexes," *Journal of Enzyme Inhibition*, 1998, 13, 177-194.

Surks, M.I. et al., "Effect of Zinc(II) and Other Divalent Cations on Binding of 3,5,3'-Triiodo-L-thyronine to Nuclear Receptors from Cultured GC Cells," J. Biol. Chem., 1989, 264, 9820-9826.

Sweeney, D. et al., "Antidiabetic and Antimalarial Biguanide Drugs are Metal-Interactive Antiproteolytic Agents," *Biochemical Pharmacology*, 2003, 66, 663-677.

Turel, I.; Bukovec, N., "Complex Formation Between Some Metals and a Quinolone Family Member (Ciprofloxacin)," *Polyhedron*, 1996, 15, 269-275.

Ungerstedt, J.S.; Sowa, Y.; Xu, W.S.; Shao, Y.; Dokmanovic, M.; Perez, G.; Ngo, L.; Holmgren, A.; Jiang, X.; Marks, P.A., "Role of Thioredoxin in the Response of Normal and Transformed Cells to Histone Deacetylase Inhibitors," *Proc. Natl. Acad. Sci.*, 2005, 102, 673-678.

Valenti et al., "The Effect of Saturation with $Zn^{2+}$ and Other Metal Ions on the Antibacterial Activity of Ovotransferrin," *Medical Microbiology and Immunol.*, 1987, 176, 123-130.

Vedejs, E. et al., "Dual Activiation in the Esterification of Hindered Alcohols with Anhydrides Using $MgBr_2$ and a Tertiary Amine," *Journal of Organic Chemistry*, 1996, 61, 5702-5703.

Walker et al., *Journal of the American Chemical Society*, 1973, 95, 3015-3017.

(56) References Cited

OTHER PUBLICATIONS

Watanabe, T., et al., "Losartan Metabolite EXP3179 Activates Akt and Endothelial Nitric Oxide Synthase via Vascular Endothelial Growth Factor Receptor-2 in Endothelial Cells," *Circulation*; 112; 1798-1805 (2005).

Wessels, J.M.; Ford, W.E.; Szymczak, W.; Schneider, S., "The Complexation of Tetracycline and Anhydrotetracycline with $M_g^{2+}$ and $Ca^{2+}$: A Spectroscopic Study," Journal of Physical Chemistry, B, 1998, 102, 9323-9331.

Wiech, N.L.; Fisher, J.F.; Helquist, P.; Wiest, O., "Inhibition of Histone Deacetylases: a Pharmacological Approach to the Treatment of Non-Cancer Disorders," *Curr. Top. Med. Chem.*, 2009, 9, 257-271.

Wilkinson, R., "Absorption of Calcium, Phosphorus and Magnesium," in *Calcium Phosphate and Magnesium Metabolism*, ed. Nordin, B.E.C.; Churchill Livingstone, Edinburgh, 1976, 106.

Williamson, D.E.; Everett, G.W., "A Proton Nuclear Magnetic Resonance Study of the Site of Metal Binding in Tetracycline," *Journal of the American Chemical Society*, 1975, 97, 2397-2405.

Winter, C.H. et al., "Synthesis and Characterization of Cyclopentadienyl Thiolato Complexes of Magnesium," *Journal of Organometallic Chemistry*, 2003, 669, 37-43.

Winter, C.H. et al., "Synthesis, Structure and Properties of Magnesium Complexes Containing Cyclopentadienyl and Amidinate Ligand Sets," *Journal of Organometallic Chemistry*, 2003, 682, 224-232.

Xia et al., "Synthesis and Characterization of Cyclopentadienyl Thiolato Complexes of Magnesium," *Journal of Organometallic Chemistry*, 2003, 669, 37-43.

Xia et al., "Synthesis, Structure, and Properites of Magnesium Complexes Containing Cyclopentadienyl and Amidinate Ligand Sets," *Journal of Organometallic Chemistry*, 2003, 682, 224-232.

Doluisio, James T., et al. "Metal complexation of the tetracycline hydrochlorides," *Journal of Medicinal Chemistry* 6:16-20 (1963).

Jezowska-Bojczuk, Malgorzata, et al., "Metal ion-tetracycline interactions in biological fluids. 10. Structural investigations on copper(II) complexes of tetracycline, oxytetracycline, chlortetracycline, 4-(dedimethylamino) tetracycline, and 6-desoxy-6-demethyltetracycline and discussion of their binding modes," *Inorganic Chemistry* 32(4):428-437 (1993).

Kisker, Caroline, et al., "The complex formed between Tet repressor and tetracycline-Mg2+ reveals mechanism of antibiotic resistance," *Journal of Molecular Biology* 247(2):260-280 (1995).

Lambs, L., et al., "Metal ion-tetracycline interactions in biological fluids. Part 4. Potential influence of calcium and magnesium ions on the bioavailability of chlortetracycline and demethylchlortetracycline, as expected from their computer-simulated distributions in blood plasma," *Inorganica Chimica Acta* 106(3):151-158 (1985).

Martin, S. R., "Equilibrium and kinetic studies on the interaction of tetracyclines with calcium and magnesium," *Biophysical Chemistry* 10(3-4):319-326 (1979).

Evans, P.A., "Modern Rhodium-Catalyzed Organic Reactions," Weinheim, Germany, Wiley-VCH, 486 pages (2005).

Barba-Behrens, N., et al., "Novel coordination compounds of quinic acid. X-reay diffraction study of copper(II) complexes where the metal ion was a chiral centre," *Trans. Metal Chem.*, 19(6):575-581 (1994).

Crabtree, R., "The Organometallic Chemistry of the Transition Metals," John Wiley & Sons Inc., NY, NY (3rd edition) (2001).

Farkas, et al., "Studies on transition-metal-peptide complexes. Part 8. Parent and mixed-ligand complexes of histidine-containing dipeptides," *J. Chem. Soc. Dalton Trans.*, pp. 1545-1551 (1983).

Rajapakse, C. S. K., et al., "Synthesis, characterization, and in vitro antimalarial and antitumor activity of new ruthenium(II) complexes of chloroquine," *Inorg. Chem.*, 48:1122-1131 (2009).

Wikipedia entry: "Organometallic chemistry" and all references and hyperlinks contained therein [online]. Apr. 13, 2010 (Apr. 13, 2010). Retrieved from the Internet using the "Internet Archive Wayback Machine" using a sparkpoint capture date of Apr. 13, 2010:<URL:http://web.archive.org/web/20100413058125/http://en.wikipedia.org/wiki/Organometallic_chemistry>.

Farkas, E., et al., "A comparison between the chelating properties of some dihydroxamic acids, desferrioxamine B and acetohydroxamic acid," *Polyhdedron*, 18(18):2391-2398 (1999).

Farkas, E., et al., "Coordination modes of hydroxamic acids in copper (II), nickel (II) and zinc (II) mixed-ligand complexes in aqueous solution," *Polyhedron*, 19(14):1727-1736 (2000).

Kurzak, B., et al., "Hydroxamic and aminohydroxamic acids and their complexes with metal ions," Coord. Chem. Rev., 114(2):169-200 (1992).

O'Brien, E.C., et al., "Metal complexes of salicylhydroxamic acid (H 2 Sha), anthranilic hydroxamic acid and benzohydroxamic acid. Acrystal and molecular structure of [Cu (phen) 2 (Ci)] Ci H 2 Sha, a model for a peroxidase-inhibitor complex," J. Inorg. Biochem., 79(1):47-51 (2000).

Zitzman et al., "Divalent metal complexes of purines. Preparation of copper (II), zinc (II) and cadmium (II) complexes of theophylline in ammonia and methylamine," *J. Inorg. Nucl. Chem.*, 40(3):571-572 (1978).

* cited by examiner pKa = 9.2
log D7.4 = 1.46
oral bioavailability = 43%
BCS Class = IV
solubility = 0.1 mg/mL at 25 °C

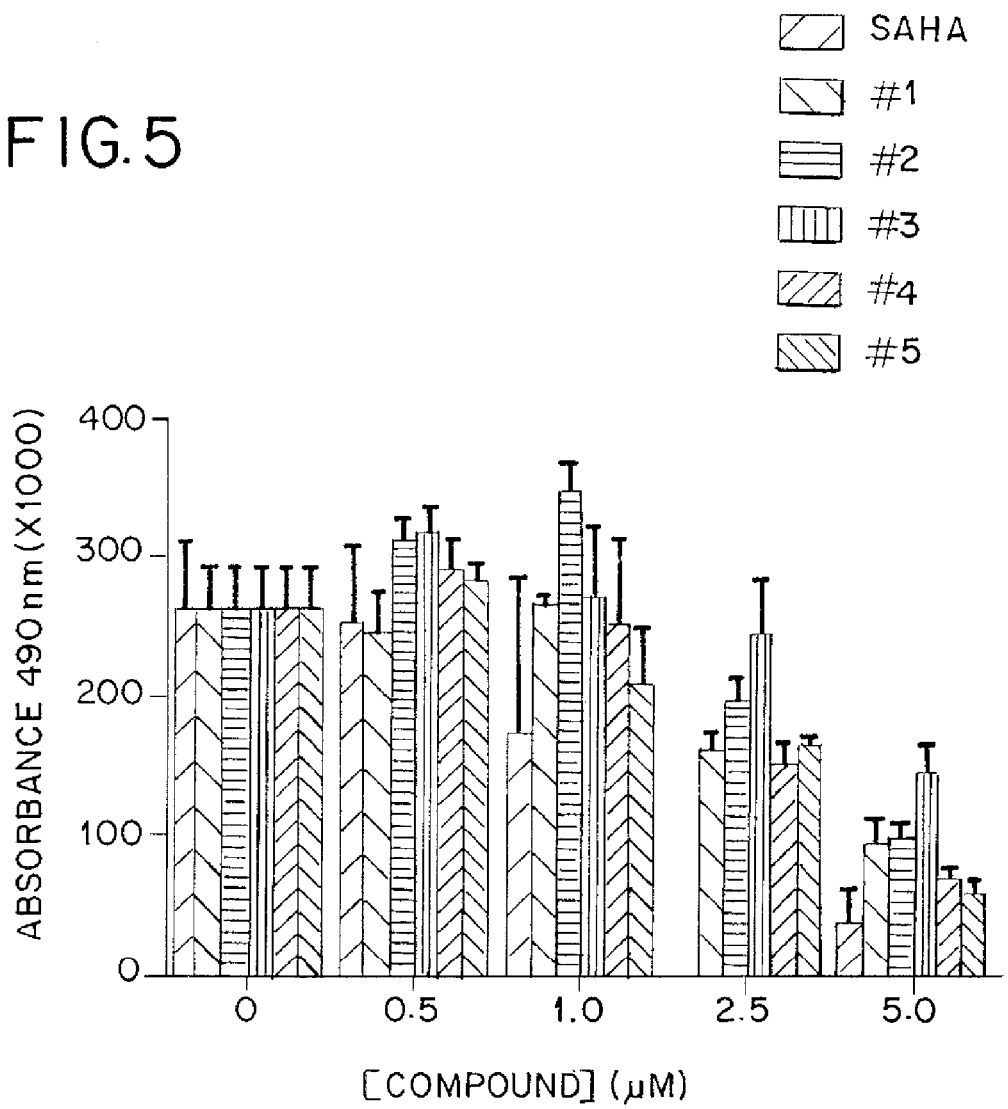

COORDINATION COMPLEXES, PHARMACEUTICAL SOLUTIONS COMPRISING COORDINATION COMPLEXES, AND METHODS OF TREATING PATIENTS

RELATED APPLICATIONS

The present application is a continuation of U.S. patent application Ser. No. 12/788,073, filed May 26, 2010, which is a continuation-in-part of prior U.S. patent application Ser. No. 11/824,411, filed Jun. 29, 2007, and issued on Sep. 21, 2010, as U.S. Pat. No. 7,799,937, which is a continuation-in-part of prior application Ser. No. 11/257,504, filed Oct. 24, 2005, which claims the benefit of U.S. Provisional Application No. 60/621,747, filed Oct. 25, 2004. The entire contents of all of these documents are incorporated herein by reference, except that in the event of any inconsistent disclosure or definition from the present specification, the disclosure or definition herein shall be deemed to prevail.

TECHNICAL FIELD

The present teachings relate generally to metal coordination complexes and methods for their therapeutic use in the treatment of patients.

BACKGROUND

The therapeutic efficacy of pharmaceutical agents is oftentimes diminished as a result of their inadequate solubilities at physiological pH. In addition, the ability to administer some pharmaceutical agents in aqueous solution—for example, via intraperitoneal (I.P.) injection, intramuscular (I.M.) injection, intravenous (I.V.) injection, and the like—is oftentimes not practicable due to the inadequate solubilities of the pharmaceutical agents at the requisite concentrations and/or pH.

As a consequence of such inadequate solubilities, it is oftentimes necessary to restrict the formulation of pharmaceutical agents to peroral dosage forms. However, when oral administration is not feasible, practical or otherwise desirable (e.g., in the treatment of patients who are unable to swallow—such as neonates—as well as critically ill, paralyzed, and/or comatose patients), the inability to administer the pharmaceutical agent in a parenteral dosage form is an acute problem.

A further limitation on the parenteral administration of pharmaceutical agents is observed in connection with compounds having high $pK_a$ values. Since pharmaceutical agents having high $pK_a$ values typically form solutions with pH values that are above the level at which one could safely or conveniently administer the drug, parenteral administration of such pharmaceutical agent is oftentimes not an option. Indeed, there are presently very few options available for formulating solutions of pharmaceutical agents with high $pK_a$ values.

In short, it would be highly desirable to (a) enhance the aqueous solubilities of poorly soluble pharmaceutical agents in order to increase their utilities or availabilities at physiological pH, and/or to (b) buffer the acidities of pharmaceutical agents to acceptable physiological levels without compromising their therapeutic efficacies.

SUMMARY

The scope of the present invention is defined solely by the appended claims and is not affected to any degree by the statements within this summary.

A first coordination complex includes a metal and a biologically active agent. The coordination complex has a $pK_a$ that is less than a $pK_a$ of the biologically active agent and the $pK_a$ of the coordination complex is physiologically acceptable, with a proviso that when the biologically active agent is suberoylanilide hydroxamic acid, the metal is neither iron nor zinc.

A second coordination complex includes a metal other than iron or zinc and a biologically active agent. The coordination complex has a $pK_a$ that is less than a $pK_a$ of the biologically active agent, and the $pK_a$ of the coordination complex is physiologically acceptable.

A third coordination complex includes a metal selected from the group consisting of magnesium, calcium, and nickel; and a biologically active agent. The coordination complex has a $pK_a$ that is less than a $pK_a$ of the biologically active agent, and the $pK_a$ of the coordination complex is physiologically acceptable.

A fourth coordination complex includes a metal selected from the group consisting of magnesium, calcium, and nickel, and a biologically active agent selected from the group consisting of a sulfamate, a hydroxamic acid, and a dihydropyridine calcium channel blocker. The coordination complex has a $pK_a$ that is less than a $pK_a$ of the biologically active agent, and the $pK_a$ of the coordination complex is less than about 9.

A fifth coordination complex includes a metal and a biologically active agent, wherein water solubility of the coordination complex is greater than water solubility of the biologically active agent at physiological pH, and wherein the $pK_a$ of the coordination complex is physiologically acceptable. When the biologically active agent is suberoylanilide hydroxamic acid, then the metal is not a transition metal unless the coordination complex further comprises a buffering ligand.

A pharmaceutical solution for treating a patient includes a coordination complex of a type described herein and water. The coordination complex is at least partially soluble in the water at physiological pH in a therapeutically efficacious concentration.

A method for treating a patient includes administering a pharmaceutical solution of a type described herein to a patient in need of the biologically active agent thereof.

BRIEF DESCRIPTION OF THE DRAWINGS

FIG. 5 shows a plot of data from breast cancer cell proliferation assays.

DETAILED DESCRIPTION

Figure 1:
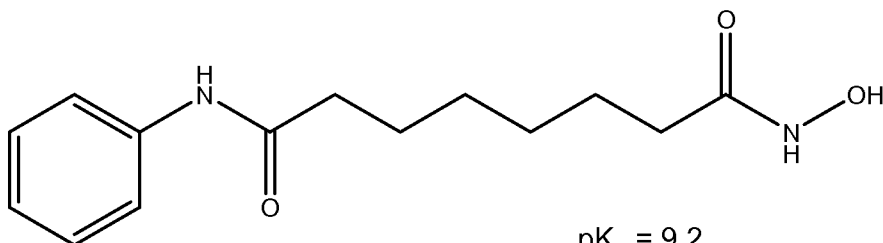
FIG. 1 shows the molecular structure and biopharmaceutical properties of suberoylanilide hydroxamic acid (SAHA).

As further described below, the inventors have discovered that coordinating a metal to a biologically active agent in a non-aqueous system favors the formation of a coordination complex—as opposed to a salt—and that the resultant coordination complex—unlike the corresponding salt—exhibits a surprising and unexpected buffering effect. It has been discovered that as a result of this buffering effect, the biologically active agent can remain soluble in water at physiological pH for a period of time sufficient for the preparation of a safe and convenient parenteral (e.g., I.V.) formulation and/or for delivering the biologically active agent to its target in the body. Thus, the coordination complexes described herein resolve the above-described problems associated with drugs having poor water solubilities that heretofore could not safely be converted to injectable forms or that exhibited diminished bioavailabilities due to their inabilities to migrate to their target sites in the allotted time. The inventors have further discovered, surprisingly and unexpectedly, that the additional coordination of a buffering ligand or adjuvant to a metal complexed with a biologically active agent—in stark and dramatic contrast to what is observed in the case of salts—provides additional buffering capacity and further lowers the pH and/or increases the solubility of the entire metal coordination complex, as further described below.

Throughout this description and in the appended claims, the following definitions are to be understood:

The phrases "coordination complex," "metal coordination complex," and the like refer to a complex of an organic compound with a metal that can be empirically differentiated from a simple metal salt of the organic compound based on physiochemical and/or spectroscopic properties, with a coordination complex typically having enhanced covalency as compared to a salt. Without wishing to be bound by a particular theory or to in any way limit the scope of the appended claims or their equivalents, it is presently believed that a "coordination complex" in the sense used herein involves a combination of coordinate covalent bonds and/or ionic bonds, whereas a metal salt is based on a purely electrostatic attraction between a cation (e.g., a metal) and an anion (e.g., an ionized form of a biologically active agent). As used herein, the phrase "coordination complex" also includes molecules that lack an ionic component (e.g., such as a neutral coordination complex prior to deprotonation, where $pK_a$ of the coordination complex falls within a physiologically acceptable range).

The phrase "physiologically acceptable" and the like as used in reference to $pK_a$ values refer to $pK_a$ values of compounds that—when dissolved—result in solutions having a pH value in a range from about 5 to about 9. It is to be understood that the $pK_a$ value per se of a compound may or may not lie in this range although the pH of the resultant solution does.

The phrase "physiological pH" refers to the pH of a patient's blood. Typically, this pH is slightly basic (e.g., approximately 7.4).

The phrase "biologically active agent" refers generally and without limitation to any compound that triggers—either directly or indirectly—a physiological response in a patient, desirably though not necessarily a therapeutically efficacious response. As used herein, the phrase "biologically active agent" is used interchangeably with the phrase "pharmaceutical agent" and the term "drug."

By way of general introduction, a coordination complex in accordance with the present teachings includes a metal and a biologically active agent. The coordination complex has a $pK_a$ that is physiologically acceptable and less than a $pK_a$ of the biologically active agent.

In some embodiments, the water solubility of the coordination complex is greater than that of the biologically active agent at physiological pH and/or is greater than that of a metal salt of the biologically active agent at physiological pH. In some embodiments, the biologically active agent exhibits therapeutic efficacy against one or more diseases, and at least a portion of the therapeutic efficacy is retained in the coordination complex. It is to be understood that liberation of the biologically active agent from the coordination complex may or may not be a prerequisite to releasing a therapeutic efficacy of the drug (in other words, the free biologically active agent and the coordination complex that contains a metal-coordinated version of the biologically active agent may each exhibit its own therapeutic efficacy).

According to the current invention, the structure of known biologically active molecules is modified to result in new molecules known as metal coordinated complexes. These new molecules have unexpectedly superior properties.

Chelation is a critical component in the stabilization of a metal coordinated complex. For the s-block metals, this is particularly true for calcium and magnesium. For example, it can be seen that the log $K_{eq}$ of the acetic acid-magnesium complex is 0.47. With the incorporation of a single amino group on the molecule (i.e., glycine) the log $K_{eq}$ increased to 1.34. Magnesium typically prefers chelation with oxygen over nitrogen and this effect can be seen by comparing the log $K_{eq}$ of adenine (log $K_{eq}$=2.08) with that of 6-hydroxypurine (log $K_{eq}$=6.65). Magnesium forms particularly strong bonds with oxidized phosphorus, such as phosphates, as is revealed by comparing the log $K_{eq}$ of adenosine (log $K_{eq}$=0.50) with that of adenosine-5'-monophosphoric acid (log $K_{eq}$=1.80).

In general, zinc complexes are more stable then the comparable magnesium complexes. This is particularly true if the ligand bears nitrogen or sulfur. (This may not be the case for ligands with oxygen only and even less so if the ligand is a phosphate.) Using the glycine example above, the log $K_{eq}$ for the glycine-zinc complex is 4.85. The strength of the zinc sulfur bond versus the oxygen bond is manifest in the relative log $K_{eq}$ values for the zinc complexes of hydroxypropanoic acid (log $K_{eq}$=0.86) and mercaptopropanoic acid (log $K_{eq}$=6.43). Comparisons of log $K_{eq}$ values with other metals and ligands reveal that this chelation stabilization prevails in metal coordination chemistry.

Whereas it may not be required that chelation occur to form a stable metal coordinated complex with inherent covalency, and this is particularly true with the transition metals combined with nitrogenous ligands, in most cases it is a preferred embodiment of this invention that the active agent chelate with the metal, particularly if the metal is magnesium.

It is an embodiment of this invention that the active agents that make the best candidates for complexing with magnesium and calcium are those that have a proton on a heteroatom (i.e., oxygen, nitrogen or sulfur) with a $pK_a$ slightly greater than water or lower than water and have an additional heteroatom in close proximity to the first protonated heteroatom such that it can participate in the bonding, or otherwise chelate, with the metal. Drugs that have this arrangement of functional groups are most likely going to bond with a metal, where the resultant metal coordinated active agent will be stable enough in a biological system and survive hydrolysis therein, such that the performance of the active agent will be sufficiently modulated. This hydrolytic stability imparted by multidentate ligands is supported by the fact that they can lower the $pK_a$'s of the ligand such that even amides can be deprotonated with weak bases, such as triethylamine, in the presence of coordinating metals. Therefore, active agents with protons on heteroatoms, which normally would not be ionized in typical biological pH, can have the proton replaced with a covalently coordinated metal, where covalency is enhanced by the additional chelation from participating heteroatoms. It is a preferred embodiment of this invention that at least one of the heteroatoms on the active agent that will bind to magnesium or calcium be oxygen or sulfur. Magnesium forms unusually strong bonds with phosphates and phosphonates and, therefore, it is an additional embodiment of this invention that the active agent coordinated with magnesium is an organophosphate or organophosphonate compound.

It is an embodiment of this invention that the active agents that make the best candidates for complexing with zinc and the p-block metals are the same as those with the s-block metals with the additional flexibility that if the active agent has two nitrogens, a nitrogen and a mercaptan or two mercaptans in a proper chelation arrangement, then the presence of a proton on a heteroatom is not necessary to form a stable metal coordinated complex. It is a further embodiment of this invention that transition metals have further ligation flexibility in that chelation is even less required for their covalent coordination complexes if the ligands have at least one nitrogen or mercapto group.

The active agents which are embodied in this invention can be divided into chemical classes as shown in Table 1 (actually they may be divided into combinations of chemical classes to reflect the heterogenous chelation potential). The drugs listed in Table 1 are not intended to be an exhaustive list of all drugs that satisfy the embodiment of this invention but a representation of the chemical classes that exist in pharmaceuticals and that other pharmaceuticals that are of the same class listed in Table 1 or have arrangements of atoms that is satisfied by the embodiments of this invention are also claimed by this invention.

TABLE 1

Biologically active molecules that form coordination complexes in accordance with the Invention.

| Chemical Class or Functional Group Combination | Therapeutic Classes | Drug Examples |
| --- | --- | --- |
| Guanide or diamine | Antidiabetic, AntiGERD, Antineoplastic, Antiviral, Antihypertensive | Metformin, Famotidine, Mitoxantrone, Adefovir, Hydralazine, Zanamivir |
| Amine or amide with sulfonamide | GERD, Diuretic, Antimigraine, Antidiabetic | Famotidine, Hydrochlorothiazide, Sumatriptan, Glipizde, Glyburide, Torsemide |
| Amine or amide with azole | GERD, Antiviral, antimigraine, Antiurolithic, Antihypertensive, Analgesic, Anitemetic | Lansoprazole, Zolmitriptan, Rabeprazole, Omeprazole, Esomeprazole, Ribavarin, Allopurinol, Clonidine, Granisetron |
| Amine or amide with alcohol | Antineoplastic, Antiviral, Bone resorption inhibitor, Antibiotic, Bronchodilator, Antithrombotic, Analgesic, Antihypertensive, Anxiolytic, Anticonvulsant | Mitoxantrone, Saquinavir, Alendronate, Albuterol, Ephedrine, Epinephrine, Dipyramidole, Oxycodone, Oxymorphone, Tetracycline, Minocycline, Doxycycline, Labetalol, Lorazepam, Oxazepam |
| β-diketone, α-diketone, ketophenol, α-ketoalcohol β-ketoalcohol | Antibiotic, Antineoplastic, Antiinflammatory, Multiple sclerosis treatment | Tetracycline, Minocycline, Doxycycline, Mitoxantrone, Atovaquone, Betamethasone, Paclitaxel, Docetaxel, Methylprednisolone, Prednisone, Idarubicin |
| β-ketoacid | Antibiotic | Levofloxacin, Ofloxacin, Norfloxacin |
| Ureide | Antiviral, Antiparkinsonian, Bronchodilator | Tenofovir, Acyclovir, Cabergoline, Theophylline, Valgancyclovir |
| Amine or amide with acid | Antihypertensive, Hormone replacement, Antiparkinsonian, Diuretic, Antipsoriatic, Antineoplastic, Antirheumatic, Antibiotic, Antiepileptic, Antidepressant, Analgesic | Quinapril, Ramipril, Trandolopril, Enalipril Lisinopril, Thyroxine, Liothyronine, DOPA, Furosemide, Methotrexate, Penicillin, Amoxicillin, Cefotetan, Captopril, Gabapentin, Ketorolac |
| Alcohol with azole | Angiotensin II receptor antagonist, | Losartan, |
| Phosphonate or phosphate | Bone resorption inhibitor, Antiviral | Alendronate, Etidronate, Fosamprenavir |
| Phosphonate or phosphate with amide | Antiepileptic | Fosphenytoin |
| Diol or polyol | Bronchodilator, Nutritional supplements, Contrast imager | Albuterol, Epinephrine, Myoinositol, Chiroinositol, Iodixanol |
| Mercaptan with acid | Antiasthmatic, Antibiotic | Montelukast, Cefazolin, Cefotetan |
| Mercaptan with amine or amide | Antipsychotic, Antihypertensive | Olanzapine, Captopril |

TABLE 1-continued

Biologically active molecules that form coordination complexes in accordance with the Invention.

| Chemical Class or Functional Group Combination | Therapeutic Classes | Drug Examples |
|---|---|---|
| Amine with amide | Hormone deficiency, Antibiotic | Tabimorelin, Amoxicillin, Loracarbef, Iodochlorohydroxyquin |
| Alcohol with acid | Analgesia, Cholesterol lowering, Antihypertensive Antiinflammatory | Salicylic acid, Atorvastatin, Mesalamine, Pravastatin, Sitofloxacin, Trovafloxacin |
| Dicarboxylic acid | Antineoplastic | Pemetrexed |
| Amine with N-oxide | Antialopecia agent | Minoxidil |
| Alcohol with Nitrites | Antibiotic | Metronidazole |
| Diene with alcohol, amine, amide or acid | Antiacne, Antineoplastic | Retinoic acid, Fenretinde |
| Oligonucleotide (polyureide or polyphosphate) | Gene therapy, Anti-AMD | iRNA, Pegaptanib |
| Oligopeptide (polyamide) | Immunosuppressant, Antianemic, Antiviral, Antineoplastic, Diuretic | Cyclosporin, Epoetin, Inteferon, Atrial Natriuretic Peptide, Abarelix |
| Oligosaccharide (polyol) | Anticoagulant, Antidiabetic, Antibiotic | Heparin, Acarbose, Gentamycin, Tobramycin |

GERD = Gastroesophageal Reflux Disease
AMD = Age-related Macular Degeneration

As illustrated in Table 1, a suitable biologically active moiety may have two functional heteroatom groups, each of which is capable of participating in the formation of a metal coordination bond. Further, as can be seen from Table 1, the two functional groups may be in a spatial relationship to each other to permit chelation to the same metal atom by those coordination bonds. According to a preferred embodiment, the coordination bond forms a 4 to 8 atom ring encompassing the metal and the heteroatom of the functional groups and the ring usually does not include a trans double bond.

The following discussion illustrates specific embodiments within the general principles discussed above.

Whereas it may not be required that chelation occur to form a stable metal coordinated complex with inherent covalency, and this is particularly true with the transition metals combined with nitrogenous ligands, in most cases it is a preferred embodiment of this invention that the biologically active moiety chelate with the metal, particularly if the metal is magnesium.

The biologically active moieties that have two functional heteroatom groups that are capable of participating in the formation of a stable metal coordination bond are embodied in this invention and include, but are not limited to the biologically active moieties set forth in Table 1. The biologically active moieties listed in Table 1 are not intended to be an exhaustive list of all biologically active moieties that satisfy the embodiment of this invention. The examples provided in Table 1 represent various groups of biologically active moieties that exist in pharmaceuticals or have arrangements of atoms that satisfy the embodiments of this invention.

The biologically active moieties listed in Table 1 have the attributes that make them a member of the group in which they are listed. They also have the functional groups that define that group and are in close enough proximity to each other to be able to chelate to a metal. Each group is defined by the specific combination of functional groups listed. For example, a guanide is a diamine but is also a specific kind of diamine. A guanide can actually be considered to be a triamine but since only two of the amino groups are necessary for chelating with a metal, the guanide and diamine are grouped together as a single chemical class. This is the same argument for the reason beta-diketone is grouped with beta-ketoalcohol, and diol is grouped with polyol.

Compounds that may be used in the embodiments of the invention, such as having two functional heteroatom groups and are capable of forming stable metal coordination bonds with a metal include, but are not limited to: Cladribine, Acetalzolamide, Eliprodil, (R,S)-3-(2-carboxypiperazin-4-yl)-propyl-1-phosphonic acid (CPP), Ifenprodil, (R)-4-oxo-5-phosphononorvaline (MDL 100453), Dihydroxyphenylglycine, (S)-(+)-a-amino-4-carboxy-2-methylbenzeneacetic acid (LY367385), Eglumegad (LY354740), (2S,2'R,3'R)-2-(2',3'-dicarboxycyclopropyl)glycine (DCG), Remacemide, Fingolimod, Teriflunomide, Laquinomod, Azathioprine, Clorazepate, Lorazepam, Temazepam, Rufinamide, Tiagabine, Progabide, Phenacemide, Lamotrigine, Ethoxzolamide, Zonisamide, Etoposide, Doxorubicin, Vorinostat (SAHA), Bicalutamide, 7-phenyl-2,4,6-hepta-trienal hydroxamic acid, Goserelin, Naltrexone, Fentanyl, Piritramide, Acadesine, Acarbose, Acebutolol, Acecarbromal, Acetylpheneturide, Acitretin, Adrafinil, Albendazole, Alexidine, Aliskiren, Alprenolol, Althiazide, Alvimopan, Ambuphylline, Amcamprosate, Amfenac, Amidephrine, Amidinomycin, Amiloride, 4-Amino-3-phenylbutyric acid, Aminophylline, Amlexanox, Amosulalol, Amprenavir, Arotinolol, Atorvastatin, Azidamfenicol, Baclofen, Balsalazide, Bambuterol, Bamethan, Befunolol, Benzthiazide, Betaxolol, Bevantolol, Bisantrene, Bitolterol, Brinzolamide, Bromfenac, Bromhexine, 5-Bromosalicylhydroxamic Acid, Bucillamine, Bucindolol, Bucumolol, Bufeniode, Bufetolol, Bufexamac, Buformin, Bufuralol, Bumadizon, Bunitrolol, Bupranolol, Buramate, Butanilicaine, Butazolamide, Butoctamide, Calcium N-Carbamoylaspartate, Capreomycin, Capuride, Carazolol, Carbazochrome Sodium Sulfonate, Carbimazole, Carisoprodol, Carmustine, Carteolol, Carticaine, Carubicin, Carvedilol, Catechin, Chloraminophenamide, Chlorguanide, Chlorphenesin Carbamate, Chlorproguanil, Chlorpropamide, Choline Alfoscerate, Cidofovir, Clodronic Acid, Clonixin, Cloranolol, Clorazepic Acid, Clorprenaline, Closantel, Cynarine, Dacarbazine, Delapril, Delavirdine, Denopamine, Diaziquone, 3,5-Dibromo-L-tyrosine, Diclofenac, Didanosine, Dideoxyadenosine, Digitalin, Digitoxin, Dioxethedrine, Dobutamine, Docarpamine, Docetaxel, Dorzolamide, Drotebanol, Droxidopa, Dyphylline, Ebrotidine, Ecabapide, Ecgonidine, Edatrexate, Eflornithine, Ellagic Acid, Endralazine, Enfenamic Acid, Entacapone, Epalrestat, Ephedrine, Epinephrine, Erdosteine, Ergotamine, Eritadenine, Esaprazole, Etanidazole, Ethylmethylthiambutene, Etidronic Acid, Etodolac, Exifone, Fenbendazole, Fendosal, Fenethylline, Fenoldopam, Fenoterol, Fenpentadiol, Fentiazac, Fepradinol, Flavopiridol, Fludrocortisone, Flufenamic Acid, Flunixin, Fluocortolone, Fluvastatin, Formoterol, Fosfosal, Gancliclovir, Gentisic Acid, Glafenine, Glibornuride, Gliclazide, Glimepiride, Glipizide, Gliquidone, Glisoxepid, Glyburide, Glybuthiazole, Guanabenz, Guanfacine, Hydrocortisone, Isoetharine, Isoflupredone, Isoladol, Lazabemide, Levobunolol, Lidamidine, Lopinavir, Lorazepam, Lormetazepani, Lotrafiban, Mefenamic Acid, Meglutol, Melagatran, Melphalan, Mepindolol, 6-Mercaptopurine, Metaproterenal, Methazolamide, Methisazone, Methocarbamol, Methoxamine, Methylergonovine, Metipranolol, Metoprolol, Midodrine, Mitoguazone, Mitoxantrone, Mivazerol, Mizoribine, Modafinil, Mopidamol, Moprolol, Moroxydine, Mycophenolate mofetil, Nadolol, Nadoxolol, Nalbuphine, Nalmefene, Naloxone, Nateglinide, Nebivolol, Nelfinavir, Nialamide, Nifenalol, Ninopterin, Nipradilol, Nitazoxanide, Nithiazide, Nolatrexed, Nordefrin, Norepinephrine, Norfenefrine, Norpseudoephedrine, Nylidrin, Octopamine, Omapatrilat, Onapristone, Orazamide, Osalmid, Orotic acid, Orthocaine, Oseltamivir, Oxazepam, Oxycinchophen, Oxyfedrine, Oxymorphone, Paclitaxel, Pamabrom, Pamidronic acid, Paramethasone, Penciclovir, Penicillamine, Perfosfamide, Phenazopyridine Hydrochloride, Pheneturide, Phenformin, Phenylephrine Hydrochloride, Phenyramidol, Phosphocreatine, Pindolol, Pipradrol, Pirarubicin, Pirbuterol, Piroxicam, Practolol, Prednylidene, Pregabalin, Prenalterol, Procaterol, Procodazole, Proglumide, Pronethalol, Propafenone, Propranolol, Protokylol, Pseudoephedrine, Quercetin, Quinocide, Raltitrexed, Rebamipide, Rebeccamycin, Reproterol, Ribavirin, Rilmazafone, Risedronic Acid, Ritodrine, Romurtide, Rufinamide, Salacetamide, Salicylamide, Sapropterin, Saquinavir, Sivelestat, Sotalol, Soterenol, Stepronin, Tafenoquine, Talinolol, Taltirelin, Tegaserod, Temazepam, Temozolomide, Tenoxicam, Terbutaline, Tertatolol, Theophylline, Thiamiprine, Thioguanine, Tiaprofenic Acid, Tilisolol, Tilarginine, Timolol, Timonacic, Tioclomarol, Tixocortol, Tocainide, Tolazamide, Tolbutamide, Tolcyclamide, Tolfenamic Acid, Toliprolol, Tolrestat, Torsemide, Tretoquinol, Triamcinolone, Tulobuterol, Ubenimex, Velnacrine, Vidarabine, Vigabatrin, Voglibose, Xamoterol, and Zoledronic Acid. Each compound listed above has other chemical properties that may require special conditions during the complexation reaction. The list of biologically active moieties and examples set forth herein provide a general protocol for the biologically active moieties listed and those related therein, but minor modifications to the applicable general protocols may be necessary for specific drugs, but are within the ordinary skill in the art.

Preferably, compounds that may be used in the embodiments of the invention, such as having two functional heteroatom groups and are capable of forming stable metal coordination bonds with a metal include, but are not limited to: Acetalzolamide, Vorinostat, Aliskiren, Alvimopan, Bicalutamide, Baclofen, Balsalzide, Brinzolamide, Chlorproguanil, Diclofenac, Dorzolamide, Droxidopa, Clonixin, Ebrotidine, Enfenamic acid, Ethylmethylthambutene, Etodolac, Flufenamic acid, Fosfosal, Lazabemide, Mefenamic acid, 6-Mercaptopurine, Melagatran, Mycopheolate mofetil, Pregabalin, Quinocide, Rilmazafone, Tafenoquine, Tilarginine, Tolfenamic acid, Cidofovir, Didanosine, Dideoxyadenosine, Etidronic acid, Moroxydine, Nelfinavir, Pamidronic acid, Risedronic acid and Zoledronic acid.

In some embodiments, the metal is a group IIA metal, a p-block metal, a transition metal, a lanthanide or an actinide. In some embodiments, the metal is a group IIA metal which, in some embodiments, is magnesium, calcium or strontium. In some embodiments, the p-block metal is a group IIIA metal, a group IVA metal or a group VA metal. In other embodiments, the metal is a transition metal which, in some embodiments, is a group VIII transition metal, a group IB transition metal, a group IIB transition metal, a group IIIB transition metal, a group IVB transition metal, a group VB transition metal, a group VIB transition metal or a group VIIB transition metal. In some embodiments, the metal is a transition metal which, in some embodiments, is a group VIII transition metal. In some embodiments, the group VIII transition metal is nickel. In some embodiments, the metal is iron or zinc. In other embodiments, the metal is neither iron nor zinc.

All manner of biologically active agents are contemplated for use in accordance with the present teachings—preferably ones that have inadequate solubilities at physiological pH and/or $pK_a$ values that are physiologically unacceptable, and which could potentially benefit from metal-coordination in accordance with the present teachings. Representative agents contemplated for use include but are not limited to the following: medicaments for treating the gastrointestinal (GI) tract (e.g., antacids; reflux suppressants; antiflatulents; antidopaminergics; proton pump inhibitors (PPIs); $H_2$-receptor antagonists; cytoprotectants; prostaglandin analogues; laxatives; antispasmodics; antidiarrheals; bile acid sequestrants; opioids; and the like); medicaments for treating the cardiovascular system (e.g., β-receptor blockers; calcium channel blockers; diuretics; cardiac glycosides; antiarrhythmics; nitrate; antianginals; vasoconstrictors; vasodilators; peripheral activators; and the like); antihypertension agents (e.g., ACE inhibitors; angiotensin receptor blockers; a blockers; and the like); coagulation agents (e.g., anticoagulants; heparin; antiplatelet drugs; fibrinolytics; anti-hemophilic factors; haemostatic drugs; and the like); atherosclerosis/cholesterol inhibitors (e.g., hypolipidaemic agents; statins; and the like); medicaments that affect the central nervous system (e.g., hypnotics; anesthetics; antipsychotics; antidepressants including but not limited to tricyclic antidepressants, monoamine oxidase inhibitors, selective serotonin reuptake inhibitors, etc.; and the like); antiemetics; anticonvulsants; antiepileptics; anxiolytics; barbiturates; movement disorder drugs including but not limited to those for treating Parkinson's disease, etc.; stimulants including but not limited to amphetamines; benzodiazepines; cyclopyrrolones; dopamine antagonists; antihistamines; cholinergics; anticholinergics; emetics; cannabinoids; 5-HT serotonin antagonists; and the like); analgesics (e.g., nonsteroidal antiinflammatory drugs or NSAIDs; opioids; various orphan drugs including but not limited to paracetamol, tricyclic antidepressants, anticonvulsants, etc.; and the like); medicaments for treating musculoskeletal disorders (e.g., NSAIDs including but not limited to COX-2 selective inhibitors, etc.; muscle relaxants; neuromuscular drugs; anticholinesterases; and the like); medicaments for treating the eye (e.g., adrenergic neurone blockers; astringents; ocular lubricants; mydriatics;

cycloplegics; anti-glaucoma agents including but not limited to adrenergic agonists, beta-blockers, carbonic anhydrase inhibitors/hyperosmotics, cholinergics, miotics, parasympathomimetics, prostaglandin agonists/prostaglandin inhibitors, nitroglycerin, etc.; and the like); topical anesthetics (e.g., benzocaine; butamben; dibucaine; lidocaine; oxybuprocaine; pramoxine; proparacaine; proxymetacaine; tetracaine; and the like); sympathomimetics; parasympatholytics; anti-bacterial agents (e.g., antibiotics; topical antibiotics; sulfa drugs; aminoglycosides; fluoroquinolones; and the like); antiviral drugs; medicaments for treatment of the ear, nose, and throat (e.g., sympathomimetics; antihistamines; anticholinergics; NSAIDs; steroids; antiseptics; local anesthetics; antifungals; cerumenolyti; and the like); medicaments for treating the respiratory system (e.g., bronchodilators; NSAIDs; anti-allergics; antitussives; mucolytics; decongestants; corticosteroids; β-2-adrenergic agonists; anticholinergics; steroids; and the like); medicaments for treating diseases of the endocrine system (e.g., androgens; antiandrogens; gonadotropin; corticosteroids; human growth hormone; insulin; antidiabetics including but not limited to sulfonylureas, biguanides/metformin, thiazolidinediones, insulin, etc.; thyroid hormones; antithyroid drugs; calcitonin; diphosponate; vasopressin analogues; and the like); medicaments for treating the reproductive system and urinary system (e.g., antifungals; alkalizing agents; quinolones; antibiotics; cholinergics; anticholinergics; anticholinesterases; antispasmodics; 5-α reductase inhibitor; selective α-1 blockers; sildenafils; fertility medications; and the like); contraceptives (e.g., hormonal contraceptives; and the like); medicaments for use in obstetrics and gynecology (e.g., NSAIDs; anticholinergics; haemostatic drugs; antifibrinolytics; hormone replacement therapy (HRT); bone regulators; β-receptor agonists; follicle stimulating hormone; luteinizing hormone; luteinizing-hormone-releasing hormone (LHRH); gonadotropin release inhibitor; progestogen; dopamine agonists; oestrogen; prostaglandins; gonadorelin; diethylstilbestrol; and the like); medicaments for treating the skin (e.g., emollients; anti-pruritics; antifungals; disinfectants; scabicides; pediculicides; tar products; vitamin A derivatives; vitamin D analogues; keratolytics; abrasives; systemic antibiotics; topical antibiotics; hormones; desloughing agents; exudate absorbents; fibrinolytics; proteolytics; sunscreens; antiperspirants; corticosteroids; and the like); medicaments for treating infections and infestations (e.g., antibiotics; antifungals including but not limited to imidazoles, polyenes, etc.; antileprotics; antituberculous drugs; antimalarials; anthelmintics; amoebicides; antivirals; antiprotozoals; antiparasitics; and the like); anti-inflammatory agents (e.g., NSAIDs; corticosteroids; and the like); medicaments for treating the immune system (e.g., vaccines; immunoglobulins; immunosuppressants; interferons; monoclonal antibodies; and the like); medicaments for treating allergies (e.g., anti-allergics; antihistamines; NSAIDs; mast cell inhibitors; and the like); nutritional agents (e.g., tonics; iron preparations; electrolytes; parenteral nutritional supplements; vitamins; anti-obesity drugs; anabolic drugs; haematopoietic drugs; food product drugs; and the like); anti-neoplastic agents (e.g., cytotoxic drugs; therapeutic antibodies; sex hormones; aromatase inhibitors; somatostatin inhibitors; recombinant interleukins; G-CSF; erythropoietin; and the like); euthanaticum agents; and the like; and combinations thereof.

In some embodiments, the biologically active agent is selected from the group consisting of an anticonvulsant, an antineoplastic, and a calcium channel blocker. In some embodiments, the anticonvulsant is a sulfamate which, in some embodiments is topiramate (sold under the tradename TOPAMAX by Ortho-McNeil Neurologics). In some embodiments, the antineoplastic is a histone deacetylase (HDAC) inhibitor which, in some embodiments, is a hydroxamic acid. In some embodiments, the hydroxamic acid is suberoylanilide hydroxamic acid, which is also known by its generic name, vorinostat, and which is sold under the tradename ZOLINZA by Merck Sharp & Dohme Corp. In embodiments in which the biologically active agent is suberoylanilide hydroxamic acid, then the metal is neither iron nor zinc. In some embodiments, the calcium channel blocker is a dihydropyridine (DHP) calcium channel blocker which, in some embodiments, is nisoldipine (sold under the tradename SULAR), nifedipine (sold under the tradenames ADALAT, NIFEDICAL, and PROCARDIA), isradipine (sold under the tradenames DYNACIRC and PRESCAL) or amlodipine (sold under the tradename NORVASC).

In some embodiments, the $pK_a$ of the coordination complex is less than about 9, and in some embodiments the $pK_a$ of the coordination complex is in a range from about 5 to about 9. In some embodiments, the range is from about 6 to about 9. In some embodiments, the range is from about 6 to about 8.5.

In some embodiments, the coordination complex further includes a buffering ligand, as explained below. In some embodiments, the $pK_a$ of the coordination complex is lower when the coordination complex contains the buffering ligand than when the coordination complex does not. In some embodiments, the water solubility of the coordination complex is greater when the coordination complex contains the buffering ligand than when the coordination complex does not. In some embodiments, the buffering ligand provides additional stability to the entire coordination complex that prevents the coordination complex from converting to a salt.

In some embodiments, the buffering ligand includes one or more hydrogen bonding sites and, in some embodiments, the buffering ligand is selected from the group consisting of an amino acid, a peptide, a carbohydrate, and a Good's buffer (e.g., MES, ADA, PIPES, ACES, cholamine chloride, BES, TES, HEPES, acetamidoglycine, tricine, glycinamide, and bicine). In some embodiments, the amino acid is arginine, lysine or histidine. In some embodiments, the buffering ligand is quinic acid, bicine, tricine, ascorbic acid or carnosine.

By way of further general introduction, a pharmaceutical solution for treating a patient includes a coordination complex of a type described above and water. The coordination complex is at least partially soluble in the water at physiological pH in a therapeutically efficacious concentration. In some embodiments, the coordination complex is soluble at least for a time sufficient to deliver the biologically active agent to a target site in the patient's body.

Finally, by way of further general introduction, a method for treating a patient includes administering a pharmaceutical solution of a type described above to a patient in need of the biologically active agent therein. In some embodiments, the pharmaceutical solution is administered to the patient by I.P. injection, I.M. injection or I.V. injection. In some embodiments, the method includes treating a neonatal seizure and the biologically active agent is topiramate. In some embodiments, the method includes treating a cancer and the biologically active agent is suberoylanilide hydroxamic acid.

Building upon the preceding general introduction to coordination complexes, pharmaceutical compositions, and methods in accordance with the present teachings, a more detailed description including specific examples is now provided solely for the purpose of illustration—not of limitation.

The present inventors have investigated the preparation of chelation compounds formed between a metal ion and polydentate drug ligands. Without wishing to be bound by a particular theory or to in any way limit the scope of the appended claims or their equivalents, it is presently believed that in these coordination complexes, the drug ligand at least partially neutralizes the positive charge of the metal ion through the formation of a combination of ionic and coordinate covalent bonds—as opposed to the purely electrostatic attraction observed in salts. While electrostatic attraction can also exist in coordination complexes, the complexes additionally have an inherently covalent coordination bond between the metal and drug ligand. It is presently believed that this enhanced covalency of the coordination complex is primarily responsible for reducing the $pK_a$ of its acidic protons, such that solutions of these coordination compounds are stable at physiological pH.

In a first series of embodiments, the biologically active agent coordinated to a metal is topiramate. Topiramate (2,3:4,5-bis-O-isopropylidene-β-D-fructopyranose sulfamate) is an anticonvulsant drug used to treat epilepsy in children and adults. It is also approved for the treatment of seizures associated with Lennox-Gastaut syndrome and for the prophylaxis of migraines. Topiramate has exhibited effective anticonvulsant and neuroprotective properties particularly after cerebral hypoxia ischemic events, and has been used experimentally in the treatment of bipolar disorders, obesity, alcoholism, post-traumatic stress disorder, bulimia, obsessive compulsive disorder, smoking addiction, and neuropathic pain. In some embodiments, when the biologically active agent is topiramate and the patient to be treated is a premature infant with an immature GI tract, the metal of the coordination complex is magnesium.

Autism symptoms often appear between the ages of 1 and 1%, which suggests that causes occur either prenatally or perinatally. Contributing factors at birth may include prematurity, lack of oxygen to the brain, prolonged labor or infections. In addition, low Apgar scores have been associated with autism, and this association is connected to preterm births. Thus, in some embodiments, a metal coordinated topiramate in accordance with the present teachings is delivered intravenously to a pre-term infant exhibiting low Apgar scores in order to help prevent the onset of autism.

Currently, topiramate is available only in an orally administered formulation, which limits its usefulness in situations where oral administration is not feasible or is otherwise undesirable. Solutions of the drug are impractical due to the hydrolytic lability of neutral topiramate in water. At present, one of the biggest limitations on the use of oral formulations of topiramate is in the treatment of neonates. Even if an I.V. solution could be formulated in an appropriately low volume for a 2-kg newborn baby, hydrolysis is likely to render the product too unstable to be practical. In addition to neonates, an I.V. formulation of topiramate would be useful for treating (a) patients who, like neonates, are unable to swallow; (b) patients with disturbed absorption from the GI tract; (c) patients who are undergoing GI surgery; and (d) patients in need of a rapid bolus of the drug. Therefore, it would be highly desirable to formulate an aqueous solution of some form of topiramate in a high enough concentration and a low enough pH to enable safe I.V. administration.

Alkaline solutions of topiramate stabilize the compound and prevent its hydrolysis. Alkaline salts of topiramate have shown promise in pre-clinical studies in neonatal pigs but no successful clinical trials have been reported. Although the solubility of topiramate salts is greatly increased relative to the neutral drug (3.59 M vs. 0.029 M), the pH of a 0.19 M solution of the salt is quite high (>10), making these salts unsuitable for many medical applications. In U.S. Pat. No. 7,351,695 granted to Ortho-McNeil, Mg, Ca, and Zn compounds of topiramate are described but without mention of their detailed structures or aqueous solubilities. Investigation by the present inventors has revealed these compounds to be salts.

Although an I.V. formulation of topiramate has yet to be developed as a therapeutic option for patients, there has been a clinical trial in which a cyclodextrin (CD) has been used to enhance the solubility of neutral topiramate. However, the potential cost of a CD derivative together with ongoing regulatory and toxicology concerns over I.V. CD in neonates may significantly limit CD's potential to address the need for an I.V. formulation of topiramate.

Topiramate has a $pK_a$ value of 8.7 due to its weakly acidic sulfamate group. The water solubility of topiramate is about 9.8 mg/mL (0.029 M) at 23° C. but increases to about 1300 mg/mL (3.59 M) for sodium topiramate trihydrate. It has been found that coordination of the topiramate anion with a suitable metal leads to increased aqueous solubility at lower physiological pH.

In accordance with the present teachings, a metal coordinated topiramate is used to formulate an aqueous solution of topiramate in a high enough concentration and a low enough pH to allow for safe I.V. administration. In some embodiments, the metal coordinated topiramate provides a heretofore unavailable treatment for neonatal seizures and related disease states.

In general, the preferred route of administration of most drugs is oral, with drug developers preferring to market oral dosage forms based on their cost, safety, and practicality. In most instances, the disadvantages of oral drug formulations (e.g., decreased and highly variable bioavailability) are mitigated by their advantages. One notable exception is that chemotherapy agents are traditionally administered parenterally in a physician's office or clinic. Taking oral doses outside such controlled settings increases risks and requires patients and caregivers to assume significantly greater responsibilities.

In a second series of embodiments, the biologically active agent coordinated to a metal is an antineoplastic agent which, in some embodiments, is suberoylanilide hydroxamic acid (SAHA). SAHA, which is shown in FIG. 1, was the first inhibitor of HDAC to be approved by the FDA and is presently indicated for the treatment of cutaneous manifestations of cutaneous T-cell lymphoma (CTCL) in patients with progressive, persistent or recurrent disease on or following two systemic therapies. Since its approval in October 2006, SAHA has also been found to be useful in the treatment of other cancers alone and in combination with other drugs or radiation therapy. Although HDAC inhibitors show utility in the treatment of cancers, it is to be understood that HDAC inhibitors may also find use in non-cancer disease states.

The oral bioavailability of SAHA is less than 50% and highly variable. Nausea and vomiting—common symptoms of the disease and all too common adverse side effects of many antineoplastics—among patients exacerbates the variability in this drug's bioavailability and further complicates its oral administration. At present, however, SAHA is marketed by Merck only as an oral capsule (100 mg). An I.V.

formulation would provide certain advantages over peroral formulations, especially with cancer and other patients that may suffer from GI upset.

SAHA is a relatively lipophilic molecule having limited water solubility of about 0.1 mg/mL. In a prior study aimed at increasing its solubility, the sodium salt of SAHA was prepared at Memorial Sloan Kettering Cancer Center but required solution pH values above 11—that is, two units above the maximum pH level (~9) usually observed for intravenous dosing—in order to stay in solution. In addition, the solution required slow administration over a two hour period in order to provide sufficient dilution to minimize irritation at the injection site.

In another study, workers used 2-hydroxypropyl-β-cyclodextrin (HOP-β-CD) at a molar concentration five times that of SAHA in an effort to enhance the latter's aqueous solubility and to enable administration of the drug in drinking water. However, cyclodextrins are expensive and not as biologically friendly as simple pH adjustment. In addition, there remains skepticism within regulatory agencies—particularly the FDA—concerning the intravenous use of cyclodextrins.

Hydroxamic acid HDAC inhibitors typically have a $pK_a$ value of about 9.2. In accordance with the present teachings, a metal coordinated SAHA is used to formulate an aqueous solution of SAHA in a high enough concentration and a low enough pH to allow for safe I.V. administration. As shown in an Example below, the solubility of SAHA in water at near physiological pH was increased ~19-fold for a Ca(SAHA)(quinic acid) analog. Moreover, as further shown in the Examples below, it has been discovered that any change in the ability of several metal coordinated SAHA analogs to inhibit breast cancer cell growth as compared to SAHA itself is negligible. Thus, the ability to deliver a wide range of doses safely and comfortably resulting in more predictable blood levels while minimizing drug exposure over long periods makes an I.V. formulation of SAHA both clinically useful and commercially valuable.

In U.S. Patent Application Publication No. 2009/0239946 A1, Merck reports a chelate complex of iron or zinc and a SAHA ligand. However, the complexes described by Merck—in contrast to those prepared in accordance with the present teachings—were not designed to have a buffering effect or to have increased solubility at physiological pH relative to SAHA itself. Thus, the metals Merck used to complex with SAHA (viz., iron and zinc) bind to SAHA too tightly to provide the increased solubility desired in accordance with the present teachings. In fact, the present inventors have found that other transition metals—not just iron and zinc—appear to bind too tightly with SAHA and result in complexes that exhibit decreased solubility, as demonstrated in an Example described below involving nickel metal. In accordance with the present teachings, it has been found that s-block metals are better suited for binding SAHA than transition metals, and are better able to impart the desired dual properties of lipid and water solubility.

However, in some embodiments, a coordination complex contains SAHA, a transition metal, and a buffering ligand. In some embodiments, the additional coordination of the buffering ligand to the transition metal confers an additional buffering capacity on the complex and further increases the solubility of the entire metal coordination complex, thereby offsetting the overly tight binding of transition metals (e.g., iron, zinc, and nickel) to SAHA that—in the absence of the buffering ligand—can result in inadequate solubilities.

In a third series of embodiments, the biologically active agent coordinated to a metal is a DHP calcium channel blocker. DHP calcium channel blockers, which are considered BCS Class II drugs, are practically insoluble in water (~1 μg/mL). Their low bioavailability is also due to extensive oxidative metabolism by cytochrome P450 enzymes in the intestinal epithelia.

The $pK_a$ of DHP calcium channel blockers typically ranges between about 9 and about 10, which means that the salts of these compounds will be soluble in water but only at a pH well above a physiologically relevant value. Lowering the pH of an aqueous solution of the salt of a DHP drug will result in its precipitation. Thus, there is a need for a formulation by which a DHP calcium channel blocker can be stabilized such that its migration from a drug delivery vehicle to a target site is facilitated sufficiently to enable maximum drug absorption.

In accordance with the present teachings, the solubility of a DHP calcium channel blocker, such as nisoldipine, is increased by forming a stable metal coordination complex thereof, which would facilitate the drug's migration from a delivery vehicle (e.g., a GEOMATRIX tablet) to the microvillus lining, after which the metal coordination complex would revert back to its neutral form due to the lower pH of between about 5 and about 6 of the aqueous unstirred layer on the surface of the microvilli. The neutralized nisoldipine would now be associated with the epithelial cell membranes and absorption of the drug could ensue. Since DHP calcium channel blockers have very similar structures and pKa values, the mechanism of stable metal coordination complex migration described above can be applied to other DHP calcium channel blockers.

The present teachings are not to be construed as being limited to a single drug delivery technology. For example, any drug delivery technology that provides controlled release of a pharmaceutical and/or targeted delivery of a drug to a specific site is contemplated for use in accordance with the present teachings. Representative technologies include but are not limited to GEOMATRIX (U.S. Pat. No. 5,422,123), cylindrical plug (U.S. Pat. No. 7,195,778), OROS®, and technologies described in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420. The entire contents of each of the above-identified U.S. patents are incorporated herein by reference, except that in the event of any inconsistent disclosure or definition from the present specification, the disclosure or definition herein shall be deemed to prevail.

In a fourth series of embodiments, a coordination complex in accordance with the present teachings further includes a buffering ligand/adjuvant. It is to be understood that in any of the embodiments described herein—regardless of the metal and/or biologically active agent (e.g., topiramate, SAHA, DHP calcium channel blocker, etc.)—a buffering ligand is optionally included in the coordination complex. In such embodiments, the biologically active agent forms a stable complex with a metal having the capacity to bind more than one ligand with at least one of the additional ligands having a pH buffering capacity. In some embodiments, the buffering ligands formally donate electrons to the metal to form an electrostatic interaction or bond and/or donate electrons through a metal coordination bond. Traditionally, chelation compounds refer to a metallic ion bonded to one or more chelating ligands, wherein a chelating ligand is a polydentate ligand capable of two or more points of attachment to the metal ion (e.g., two or more donor atoms) to form a heterocyclic ring structure.

A sulfamate, HDAC inhibitor, or DHP calcium channel blocker used as the biologically active agent of a coordination complex in accordance with the present teachings can provide a ligand in which one atom is tightly bound to the metal while other atoms provide minor contributions to metal chelation. The bond between particular metals and biologically active agents imparts some covalency—as would be conferred in a coordination complex—in addition to some ionic character—as would be conferred in a salt. The combination of these properties confers onto the coordination complex an ability to retain solubility at relatively high concentrations at physiological pH.

The solubility of coordination complexes is influenced by various interacting factors that involve composition and structure including but not limited to the nature of the metal ion, the symmetry of the molecule, the redistribution of electron density in ligands upon complexation, and/or the conformation of coordinated ligands. As a guideline, the higher the lipophilicity or hydrophilicity of the ligands involved in chelation, the higher the corresponding lipophilicity or hydrophilicity of a coordination complex.

Without wishing to be bound by a particular theory or to in any way limit the scope of the appended claims or their equivalents, it is presently believed that the lowering in pH of a coordination complex in accordance with the present teachings—whether or not the coordination complex contains a buffering ligand—involves ligand polarization enhancement.

Figure 2:
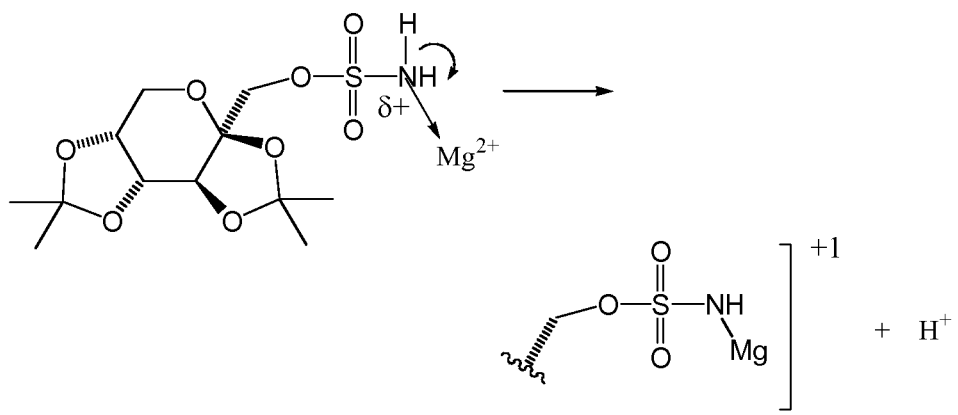
FIG. 2 shows the enhancement of ligand polarization using topiramate (tpm) as a representative ligand.

According to the theory of ligand polarization enhancement, coordination of a ligand to a positively-charged metal center will result in development of a positive charge on the ligand donor atom or functional group, such that any group attached to the donor atom capable of leaving as a cation will have its leaving group capacity enhanced through metal coordination. Thus, the $pK_a$ of protic acids will be typically lowered upon coordination (e.g., by ~2 $pK_a$ units). For example, when the biologically active agent/ligand is topiramate (tpm), the donor atom is the N atom of the sulfamate group, and the leaving cation is a proton, thereby generating the tpm⁻ ligand as shown in FIG. 2. This phenomenon—combined with the fact that weaker bases can participate in chelate forming reactions—means that metal coordination complexes form molecules that are less basic than organic salts.

In embodiments in which a buffering ligand is included in the coordination complex of a metal and a biologically active agent, the metal is selected such that other ligands can be attached to the metal:drug complex (i.e., the metal has more than 2 binding sites). In some embodiments, the metal is able to adopt a square planar or other 4-binding or 5-binding site geometry. In some embodiments, the metal is able to adopt octahedral geometry. In some embodiments, the metal is generally recognized as safe (GRAS) by the FDA. In some embodiments, the metal is magnesium, calcium, strontium or zinc.

In some embodiments, the buffering ligand is selected from a group of molecules that (a) form stable complexes or chelates with the metal and (b) have a buffering capacity such that the entire complex has a $pK_a$ within a physiological acceptable range of about 5 to about 9 (in some embodiments from about 6 to about 8.5). In some embodiments, the buffering ligand is an amino acid which, in some embodiments, is arginine, lysine or histidine.

In some embodiments in which a buffering ligand is included in the coordination complex, the metal, the biologically active agent, and the buffering ligand are part of a single molecular entity, such that the entire coordination complex retains its structural integrity at physiological pH for a period of time sufficient to allow I.V. administration and/or migration from a drug delivery vehicle to target tissue. In addition to the stability provided to the coordination complex by its ionic and coordination bonds, other forces including but not limited to hydrogen bonding and/or Van der Waals attractions—especially between the buffering ligand and the biologically active agent—can also contribute to the overall stability of the coordination complex.

In some embodiments in which the coordination complex contains a buffering ligand and the biologically active agent is topiramate or an HDAC inhibitor, the coordination complex is stable in water at least long enough for it to be injected as a solution. Thus, sterile water is added to a powder of a coordination complex containing a buffering ligand, a solution formed, and the resultant solution injected into a patient before precipitation of the complex becomes problematic. Thus, through a combination of metal coordination, buffering to lower $pK_a$, and slowed kinetics of precipitation, a coordination complex in accordance with the present teachings provides a stable, water-soluble form of a drug that would otherwise have been exceedingly difficult and/or impossible to prepare.

Figure 3:
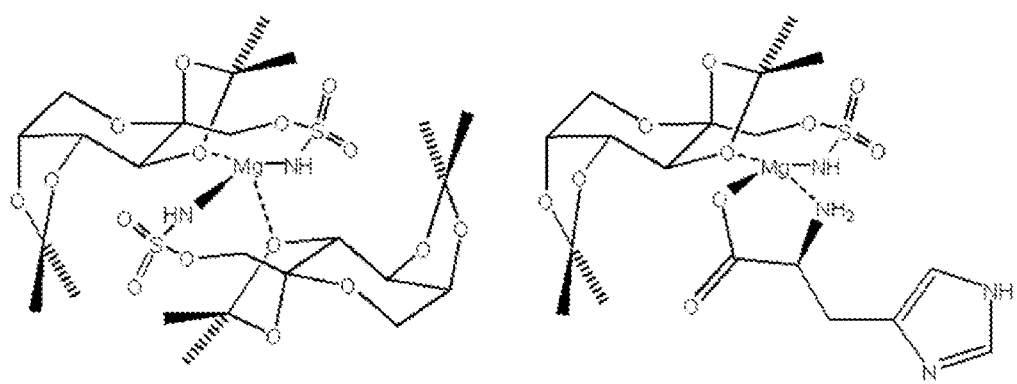
FIG. 3 shows a magnesium-coordinated topiramate [Mg(tpm)$_2$] and a magnesium-coordinated topiramate with a histidine buffering ligand [Mg(tpm)(his)].
Figure 4:
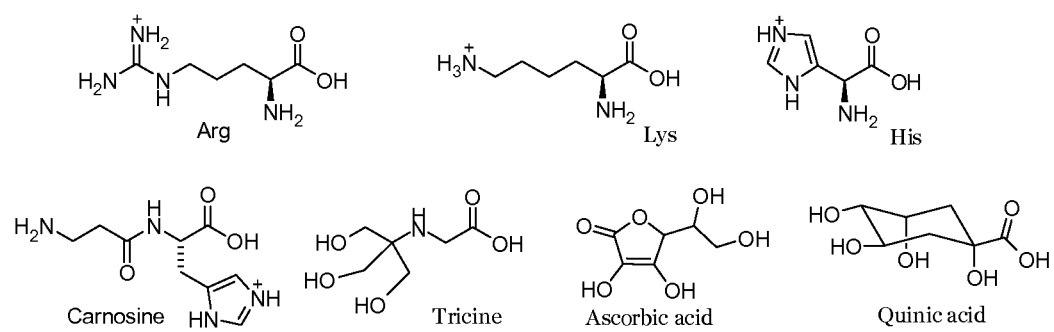
FIG. 4 shows molecular structures of representative buffering ligands.

FIG. 3 shows two coordination complexes embodying features of the present teachings in which the biologically active agent is topiramate, the metal is magnesium, and the coordination complex either lacks (i.e., the coordination complex on the left) or includes (i.e., the "mixed ligand" coordination complex on the right) a buffering ligand (e.g., the amino acid histidine). In the "mixed ligand" coordination complex shown on the right in FIG. 3, a buffering ligand (i.e., histidine) replaces one of the topiramates of the coordination complex on the left. In some embodiments, the buffering ligand is an adjuvant capable of improving the solubility of a biologically active agent at low pH. One factor that enhances the aqueous solubility of a coordination complex is its ability to hydrogen bond with a solvent. Thus, a coordination complex that contains a buffering ligand capable of forming hydrogen bonds is generally more soluble in polar protic solvents because of the increased energy of solvation. Amino acids, peptides, and carbohydrates—including but not limited to those shown in FIG. 4—are three representative types of biocompatible buffering ligands that can be used in accordance with the present teachings.

In some embodiments, the buffering ligand is an amino acid. In general, amino acids have powerful chelating properties, are readily available, and exhibit diverse physicochemical properties. In some embodiments, the amino acids are protonated at physiological pH to increase water solubility and to act as intramolecular buffers. In some embodiments, the buffering ligand is a carbohydrate. Carbohydrates are configured for enhancing the water solubility of a coordination complex, and acidic carbohydrates (e.g., ascorbic acid) are configured to lower the pH of a coordination complex in solution. In some embodiments, the biologically active agent is topiramate and the buffering ligand is ascorbic acid. In some embodiments, a coordination complex in accordance with the present teachings includes a buffering ligand wherein the buffering ligand facilitates transport of a biologically active agent to a target site (e.g., a specific organ and/or tissue) in a patient.

The synthetic route by which a coordination complex in accordance with the present teachings—whether or not it further contains a buffering ligand—is prepared is not restricted. However, for purposes of illustration, some representative approaches, which are not to be construed as limiting and/or the only available routes, are now described.

First, the preparation of a coordination complex that does not necessarily contain a buffering ligand can be achieved by a synthetic route including but not limited to the following: (1) reacting an acidic ligand having additional donor atoms with a strong base in water to form a salt, which is then reacted with a metal salt—usually in the form of a halide or an acetate—in an organic solvent; and (2) reacting an acidic ligand having additional donor atoms with a metallic base such as $Mg(t\text{-butoxide})_2$, $Ca(OMe)_2$, or $Zn(i\text{-propoxide})_2$ in an organic solvent. As further shown in the examples below, a coordination complex containing topiramate and either magnesium or zinc metal has been prepared by method (1), while a coordination complex containing topiramate and calcium metal has been prepared by method (2). Moreover, it should be noted that a key principle in favoring the formation of a coordination complex of an organic compound and a metal as opposed to a salt is to prepare the complex in a non-aqueous system, such as shown in the following representative reaction in which the biologically active agent is topiramate:

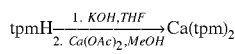

Second, in the preparation of a coordination complex that contains a buffering ligand, parameters such as stoichiometry, order of reagent addition, solvent, temperature, concentration, purity of solvents and/or reagents, and the like should be controlled. Within these parameters, the preparation of a coordination complex that contains a buffering ligand can be achieved by a synthetic route including but not limited to the following, as depicted schematically in the corresponding reactions (1)-(4) below: (1) simultaneous combination of the biologically active agent (L) and buffering ligand (L'); (2) sequential combination of the ligands L and L'; (3) coproportionation reaction between two binary bis-ligand (or homoleptic) complexes; and (4) substitution reaction in which a ligand in a metal complex is replaced by a second ligand (a reaction that depends on thermodynamic stability of the ligand binding with the metal ion and on the reaction mechanism).

$$M+L+L' \rightleftharpoons MLL' \quad (1)$$

$$ML+L' \rightleftharpoons MLL' \quad (2)$$

$$ML_2+ML'_2 \rightleftharpoons 2MLL' \quad (3)$$

$$ML_2+L' \rightleftharpoons MLL'+L \quad (4)$$

In a solution containing a metal ion and ligands L and L', the formation of the mixed ligand complex MLL' is more favored on a statistical basis than the formation of the binary complexes $ML_2$ and $ML'_2$. The equilibrium constant for the formation of the mixed ligand complex is related to the equilibrium constant of the corresponding coproportionation reaction (reaction 3 above), $K_{coprop}$. If statistical factors alone were responsible for formation of the mixed ligand complex, then $K_{coprop}$ would equal 4. However, since the experimental values of $K_{coprop}$ differ from the statistical value, other factors are involved in the formation of mixed ligand complexes. These factors include electronic, electrostatic, and steric effects that can affect product formation by stabilizing or destabilizing the complexes.

As further shown in the examples below, a coordination complex that contains topiramate as its biologically active agent and an amino acid as a buffering ligand has been prepared using the coproportionation approach, shown in reaction (3) above. Other mixed ligand coordination complexes have also been prepared using the coproportionation approach as shown in the examples below:

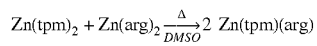

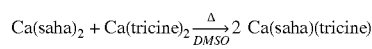

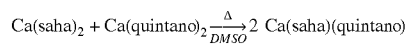

Of course, it is to be understood that the coproportionation reaction shown above is only one representative approach to preparing a coordination complex containing a buffering ligand and that other synthetic approaches are also viable.

As explained above, a coordination complex in accordance with the present teachings is different than a simple metal salt. The differentiation of coordination complexes and simple salts can be achieved by various methods including but not limited to: $^1H$ and $^{13}C$ nuclear magnetic resonance (NMR) spectroscopy; two-dimensional NMR techniques, such as Diffusion Ordered SpectroscopY (DOSY) NMR; differentiating physiochemical properties (e.g., solubility and/or distribution coefficients); infrared (IR) spectroscopy; mass spectrometry; molar conductivity; magnetic measurements; and x-ray crystallography.

Structures can be determined using $^1H$ and/or $^{13}C$ NMR spectroscopy through a comparison of chemical shifts, coupling constants, and/or changes of relaxation parameters caused by coordinate covalent bond formation as compared to a reference drug ligand (e.g., topiramate). As shown in the examples below, the magnitude of the change in chemical shift in the $^1H$ NMR spectra of a metal-coordinated topiramate is not similarly observed in the case of a simple salt.

Coordination complexes in accordance with the present teachings can be evaluated on the basis of solubility measurements, distribution coefficients, stability measurements, etc. A description of each of these types of measurement is given below.

Solubility: Intrinsic solubility ($WS_0$) is defined as the number of moles per liter of solute that dissolves into solution. Equilibrium between solute and solution is maintained at a specific temperature (usually 25° C.). For a neutral compound, the total solubility equals the intrinsic solubility because only the neutral compound is involved. However, for a compound with ionizable groups, the solubility expression is more complex because multiple species with varying solubilities are present. Accordingly, it is necessary to use the term aqueous solubility (WS) to define the solubility of compounds having ionizable groups. Aqueous solubility is the sum of the individual solubilities for the neutral compound and all ionized species present. For compounds having ionizable groups, aqueous solubility is a function of pH. Given $WS_0$ (the solubility of the neutral compound) and the solubility of each ionized species ($C_i$), the equation for aqueous solubility becomes:

$$WS = WS_0 + \Sigma [C_i]_{aq}$$

A pH-solubility profile is a set of solubility values at specified pH values. The values given in a pH profile refer to solubility as a function of pH for all species of a compound (ionizable and neutral) in solution. Solubility profiles can be used to delineate solubility in complex situations where multiple ionizable species are present.

Distribution Coefficients: Due to the inherent covalency associated with coordination complexes, penetration of the blood-brain barrier (BBB) by the coordination complex after its administration into the bloodstream is facilitated. Indeed, in some embodiments, penetration of the BBB is particularly desirable, such as in treatments for brain cancer (e.g., using a biologically active agent such as topiramate or an HDAC inhibitor). The BBB permeability of coordination complexes in accordance with the present teachings can be predicted by measuring their distribution coefficients. The distribution coefficient (D) is the ratio of un-ionized compound in the lipid phase to the total in the aqueous phase as given by:

$$D = [\text{un-ionized}](o)/[[\text{un-ionized}](aq) + [\text{ionized}](aq)]$$

The distribution coefficient is not a constant value and will vary according to the protogenic nature of the molecule. Log D ($\log_{10}$ of the distribution coefficient) at pH 7.4 is often reported to give an indication of the lipophilicity of a drug at the normal pH of blood plasma. A log D value of 2.0 is considered optimal for crossing the blood-brain barrier. For topiramate, for example, the log D value is −0.5. However, despite this relatively low value, topiramate appears to readily cross membranes.

Without wishing to be bound by a particular theory or to in any way limit the scope of the appended claims or their equivalents, it is presently believed that increasing log D by coordinating a ligand with a metal—although it may seem counterintuitive—is consistent with the formation of a coordinate covalent bond between a metal and a ligand anion, and supports a contention that metal coordination leads to amphiphilic drugs. Without wishing to be bound by a particular theory or to in any way limit the scope of the appended claims or their equivalents, it is further believed that metal coordination in accordance with the present teachings will not significantly lower a drug's log D or adversely affect its ability to penetrate the BBB. Furthermore, for a coordination complex in which the biologically active agent is topiramate, it is expected that the bond between the metal and topiramate will dissociate prior to transport across the BBB due to circulating proteins and minerals in the bloodstream. Thus, coordination complexes in accordance with the present teachings—whether or not they contain a buffering ligand—should perform within the body at least as well as the reference drug itself.

Stability: In some embodiments, a coordination complex in accordance with the present teachings (e.g., one in which the biologically active agent is topiramate) does not revert back to the biologically active agent in aqueous solution before the solution is administered to the patient. However, once the coordination complex has been delivered to the blood, it is anticipated that that the coordination complex will dissociate (although, by that point, sufficient dilution will have occurred such that the biologically active agent will remain dissolved). In typical nursing/pharmacy operations, powders are reconstituted prior to use and administered within approximately 10 minutes of dilution. In some embodiments, integrity of the coordination complex is maintained at or above 90% for at least 30 minutes.

The following examples and representative procedures illustrate features in accordance with the present invention, and are provided solely by way of illustration. They are not intended to limit the scope of the appended claims or their equivalents.

EXAMPLES

Synthesis of Calcium(topiramate)$_2$: To a 10-mL round-bottomed flask equipped with magnetic stirrer was added potassium topiramate (249.8 mg, 0.661 mmol). Anhydrous methanol (5 mL) was added via syringe and the solid dissolved. Calcium acetate (52.9 mg, 0.330 mmol) was added and dissolved with stirring. The solution was stirred at room temperature for 16 hrs. Solvent was removed under reduced pressure affording a white solid in quantitative yield. $^1$H NMR (DMSO-d$_6$): δ 4.55 (dm; J=7.8 Hz; 1H; H4), 4.29 (m; 1H; H3), 4.21 (br. d; J=8.0 Hz; 1H; H5); 3.75-3.66 (m; 3H; H1a,b,6a), 3.55 (br. d; J=13.2 Hz; 1H; H6b), 1.43 (s; 3H; CH$_3$); 1.35 (s; 3H; CH$_3$), 1.34 (s; 3H; CH$_3$), 1.27 (s; 3H; CH$_3$). Ca 4.2% (theoretical 4.4%). This material (32 mg based on topiramate) was dissolved in H$_2$O (1 mL) and the pH adjusted to 7.0 by the addition of 1.0 N HCl. No precipitate was observed upon standing for 2 hours.

As a point of reference, the $^1$H NMR data for topiramate (DMSO-d$_6$) are as follows: δ 4.61 (dd; J=7.8, 2.4 Hz; 1H; H4), 4.25 (br. d; J=8.0 Hz; 1H; H5); 4.24 (d; J=2.0 Hz; 1H; H3), 4.01 (d; J=10.0 Hz; 1H; H1a), 3.96 (d; J=10.0 Hz; 1H; H1b), 3.75 (d; J=12.8 Hz; 1H; H6a), 3.62 (d; J=12.8 Hz, 1H, H6b), 1.47 (s; 3H; CH$_3$); 1.37 (s; 3H; CH$_3$), 1.34 (s; 3H; CH$_3$), 1.28 (s; 3H; CH$_3$).

Calcium Salt of Topiramate: To a 10-mL beaker equipped with magnetic stirrer, topiramate (50 mg, 0.147 mmol) was suspended in 2 mL of water with stirring. KOH (147 μL, 147 μmol) was added as a 1.0 N aqueous solution. The topiramate mostly dissolved with gentle heating. Calcium acetate (11.63 mg, 0.0735 mmol) was added. The solution was stirred overnight. The slightly cloudy suspension was filtered to remove any unreacted topiramate. The water was removed from the filtrate under reduced pressure affording 43.7 mg of a white solid. $^1$H NMR (DMSO-d$_6$): δ 4.59 (dd; J=7.8, 2.4 Hz; 1H; H4), 4.25 (d; J=2.0 Hz; 1H; H3), 4.24 (br. m; 1H; H5); 3.96 (d; J=10.0 Hz; 1H; H1a), 3.91 (d; J=10.0 Hz; 1H; H1b), 3.75 (d; J=12.8 Hz; 1H; H6a), 3.60 (d; J=12.8 Hz, 1H, H6b), 1.46 (s; 3H; CH$_3$); 1.36 (s; 3H; CH$_3$), 1.34 (s; 3H; CH$_3$), 1.28 (s; 3H; CH$_3$).

The compound obtained displayed a $^1$H NMR differing significantly from the coordination complex especially comparing the chemical shifts of protons 1a and 1b. A sample of this material (32 mg based on topiramate) was dissolved in H$_2$O (1 mL) and the pH adjusted to 7.0 as above. A precipitate formed immediately which was identified after filtration as topiramate.

A comparison of the above results clearly shows a difference in physicochemical properties between a salt and a coordination complex.

Synthesis of Magnesium (topiramate)$_2$: To a 5-mL conical vial equipped with magnetic stirrer was added potassium topiramate (120 mg, 0.317 mmol). Anhydrous methanol (2.5 mL) was added via syringe and the solid dissolved. Magnesium acetate (37.8 mg, 0.176 mmol) was added and dissolved with stirring. The solution was stirred at room temperature for 16 hrs. Solvent was removed from the solution under reduced pressure yielding white solid. $^1$H NMR (DMSO-d$_6$): δ 4.56 (dd; J=8.0, 2.4 Hz; 1H), 4.28 (d;

J=2.4 Hz; 1H), 4.22 (br. d; J=8.0 Hz; 1H); 3.80 (d; J=14.8; 1H), 3.80 (d; J=14.8 Hz; 1H), 3.76 (d; J=14.8 Hz; 1H), 3.73 (d; J=13.2 Hz; 1H), 3.56 (d; J=13.2 Hz; 1H), 1.44 (s; 3H); 1.35 (d; J=5.2 Hz; 6H), 1.27 (s; 3H). $^{13}$C NMR (DMSO-$d_6$): δ 113.22, 113.02, 106.80, 75.33, 74.72, 72.27, 65.49, 53.73, 31.48, 30.95, 30.45, 29.23.

Synthesis of Magnesium(topiramate)(histidine): To a 1-mL ampoule were added magnesium topiramate (15.0 mg, 0.021 mmol), magnesium histidine (6.0 mg, 0.018 mmol), and water (1.0 mL) via pipette. The ampoule was sealed and heated at 100° C. for 16 hours. Solvent was removed under reduced pressure affording a white solid. $^1$H NMR; ($D_2O$): δ 7.74 (s; 1H2), 7.04 (s; 1H; H4), 4.48 (dd; J=12.8 Hz, 4.8 Hz; 1H; T4), 4.43 (d; J=2.2 (ay.); 1H; T3), 4.21 (d; J=5.2 Hz; 1H; T5), 3.99 (d; J=13.6 Hz; 1H; T6a); 3.94 (d; J=6.4; 1H; T1a), 3.92 (d; J=6.4; 1H; T1b), 3.78 (d; J=13.6; 1H; T6b), 3.67 (dd; J=26.4 Hz, 12.4 Hz; 1H; H7), 3.19 (dd; J=13.0 Hz (av.), 7.8 Hz (av.); 1H; H6a); 3.08 (dd; J=15.0 Hz (ay.), 7.0 Hz (ay.); 1H; H6b), 1.59 (s, 3H; T $CH_3$), 1.50 (s; 3H; T $CH_3$), 1.45 (s; 3H; T $CH_3$), 1.42 (s; 3H; T $CH_3$).

Synthesis of Zinc(topiramate)(arqinine): To a 5-mL vial equipped with magnetic stirrer were added zinc topiramate (25.4 mg, 0.034 mmol) and anhydrous dimethylacetamide (2.5 mL) via syringe. To this solution was added zinc arginate (14.1 mg, 0.034 mmol) and the mixture was stirred to homogenize. An aliquot (1 mL) was syringed into an ampoule, which was sealed and heated at 102° C. for 16 hours. Solvent was removed under reduced pressure affording a white solid. $^1$H NMR; (DMSO-$d_6$): δ 5.08 (m; 1H; NH), 4.57 (br d; J=8.0 Hz; 1H; T4), 4.27 (s; 1H; T3); 4.21 (d; J=8.4; 1H; T5), 3.73 (d; J=12.8 Hz; 1H; T6a), 3.54 (d; J=11.6; 1H; T6b), 3.45-3.30 (m; 3H; T1a,b A2), 3.08 (m; 2H; A5); 1.79-1.72 (m; 1H; A3a), 1.60-1.48 (m, 3H; A3b, A4a,b), 1.44 (s; 3H; T CH3), 1.34 (s; 6H; 2× T CH3), 1.27 (s; 3H; T CH3).

As a point of reference, the $^1$H NMR data for Zn(tpm)$_2$ (DMSO-$d_6$) are as follows: δ 4.56 (dd; J=7.8, 2.0 Hz; 1H; T4), 4.28 (d; J=2.0 Hz; 1H; T3), 4.22 (d; J=8.0 Hz; 1H; T5); 3.93 (d; J=10.4 Hz; 1H; T1a), 3.82 (d; J=10.4 Hz; 1H; T1b), 3.73 (d; J=12.8 Hz; 1H; T6a), 3.57 (d; J=12.8 Hz, 1H, T6b), 1.44 (s; 3H; CH3); 1.37 (s; 3H; CH3), 1.34 (s; 3H; CH3), 1.27 (s; 3H; CH3). As a point of reference, the $^1$H NMR data for Zn(arg)$_2$ (DMSO) are as follows: δ 3.34 (br s; 1H; A2), 3.12 (br s; 2H; A5a,b), 1.78 (br s; 1H; A3a), 1.56 (br s; 3H; A3b A4a,b).

Of particular significance are the observations in the $^1$H NMR of the mixed ligand coordination complex that H3 of topiramate collapses from a doublet (J=2.0 Hz) to a singlet, and that H4 collapses from a doublet of doublets to a doublet. Without wishing to be bound by a particular theory or to in any way limit the scope of the appended claims or their equivalents, it is presently believed that this is evidence of a ring conformational change caused by an intramolecular ligand-ligand interaction between topiramate and arginine in the ternary coordination complex, which is not observed for the Na, K or Ca salts or Zn coordination complex. A similar phenomenon with respect to the coupling of H3 in topiramate is observed for Ca(tpm)$_2$, the homoligated compound (binary complex), although the effect is not as large. In this case, the ligand-ligand interaction is influenced by the differential binding affinity of the metal.

Solubility/pH Studies of Topiramate-Containing Coordination Complexes: Initial screening of drug candidates was based on a qualitative determination of aqueous solubility using gravimetric methods. Briefly, a known quantity of coordination compound (ca. 50 mg) was dissolved in a known amount of water (1000/L). The pH of the resulting mixture was measured, and the solution/suspension was filtered and concentrated to afford a minimal solubility value. Using this method, it was found that the solubility of Ca(tpm)$_2$ is ≥34 mg/mL at pH 7.0 which—surprisingly and unexpectedly—is at least three times the solubility of free topiramate (9.8 mg/mL).

Synthesis of Mq(saha)$_2$: To a 25-mL round-bottomed flask equipped with magnetic stirrer, heating mantle, and reflux condenser was added saha (100 mg, 0.379 mmol). Anhydrous methanol (10 mL) was added via syringe and the solid dissolved. Magnesium acetate (40.6 mg, 0.189 mmol) was added in one portion and immediately dissolved. The solution was refluxed for 16 hrs. Solvent was removed from the clear solution under reduced pressure yielding a colorless solid. The aqueous solubility was determined by UV-VIS spectroscopy (242 nm in MeOH) to be 0.40 mg/mL at pH 7.75. $^{13}$C NMR (DMSO-$d_6$): δ 171.7, 139.8, 136.6, 129.0, 123.3, 119.4, 36.8, 28.8, 25.4. Note: The $^{13}$C NMR chemical shifts for the carbonyl carbons of SAHA are 171.7 and 169.5 ppm.

Synthesis of Ca(tricine)$_2$: Tricine (250 mg, 1.40 mmol) and water (7 mL) were added to a 10-mL vial. Barium hydroxide (133 mg, 0.70 mmol) was added to this solution in one portion. The clear solution was stirred for 30 minutes at room temperature. $CaSO_4$ (121 mg, 0.70 mmol) was added in one portion. A precipitate formed immediately. The suspension was stirred an additional 1 hour. The mixture was vacuum filtered using medium porosity filter paper. Solvent was removed under reduced pressure leaving 278 mg (0.7 mmol, 100% yield) of Ca(tricine)$_2$ as a colorless solid.

Synthesis of Ca(saha)$_2$: SAHA (50 mg, 0.19 mmol) and anhydrous methanol (2 mL) were added to a 2-mL ampoule. Calcium acetate (15 mg, 0.10 mmol) was added in one portion. The ampoule was sealed and the solution was refluxed for 16 hrs. Solvent was removed under reduced pressure leaving a colorless solid. The aqueous solubility was determined by UV-VIS spectroscopy (242 nm in MeOH) to be 0.45 mg/mL at pH 8.60.

Synthesis of Ca(saha)(tricine): Ca(saha)$_2$ (25 mg, 0.04 mmol) and anhydrous DMSO (2 mL) were added to a 2-mL ampoule. Ca(tricine)$_2$ (18 mg, 0.04 mmol) was added in one portion. The ampoule was sealed and the solution was heated at 65° C. for 16 hrs. Solvent was removed under reduced pressure leaving a colorless solid. The aqueous solubility of this compound was determined by UV-VIS spectroscopy (242 nm in MeOH) to be 1.4 mg/mL at pH 8.75.

Synthesis of Ca(quinic acid)$_2$: Quinic acid (150 mg, 0.781 mmol) and DMSO (5 mL) were added to a 25-mL round-bottomed flask. Calcium methoxide (39.8 mg, 0.391 mmol) was added in one portion. The clear solution was stirred for 16 hours at room temperature. Solvent was removed under reduced pressure leaving a colorless solid.

Synthesis of Ca(saha)(quinic acid): Ca(saha)$_2$ (20 mg, 0.035 mmol) and anhydrous DMSO (2 mL) were added to a 2-mL ampoule. Ca(quinic acid)$_2$ (15 mg, 0.035 mmol) was added in one portion. The ampoule was sealed and the solution was heated at 65° C. for 16 hrs. Solvent was removed under reduced pressure leaving a colorless solid. The aqueous solubility of this compound was determined by UV-VIS spectroscopy (242 nm in MeOH) to be 1.86 mg/mL at pH 8.25.

Synthesis of Ni(saha)$_2$: To a 25-mL round-bottomed flask equipped with magnetic stirrer, heating mantle, and reflux condenser was added SAHA (100 mg, 0.379 mmol). Anhydrous methanol (10 mL) was added via syringe and the solid dissolved. Nickel acetate (47.2 mg, 0.189 mmol) was added in one portion and dissolved with stirring. The solution was refluxed for 16 hrs. Solvent was removed from the green solution under reduced pressure yielding green solid. The aqueous solubility was determined by UV-VIS spectroscopy (242 nm in MeOH) to be 0.04 mg/mL at pH 5.86.

Solubility and pH Testing: Table 2 below shows data for the solubility of SAHA, the sodium salt of SAHA, and five metal coordinated complexes of SAHA.

TABLE 2

| Compound No. | Compound | Water Solubility (mg/mL) | pH |
|---|---|---|---|
|  | saha | 0.1 | 7.95 |
|  | Na(saha) | 0.69 | 10 |
| 1 | Mg(saha)$_2$ | 0.41 | 7.94 |
| 2 | Ca(saha)$_2$ | 0.45 | 8.6 |
| 3 | Ni(saha)$_2$ | 0.04 | 5.67 |
| 4 | Ca(saha)(tricine) | 1.41 | 8.75 |
| 5 | Ca(saha)(quinic acid) | 1.86 | 8.25 |

As shown in Table 2, the sodium salt of SAHA shows a nearly 7-fold increase in solubility over SAHA itself although the pH of the solution of this salt is 10—well above the acceptable range for an I.V. formulation. However, surprisingly and unexpectedly, metal coordination of SAHA with an s-block metal increased its solubility to approach that of the unusable sodium salt but at a much lower, physiologically acceptable pH. Moreover, incorporating adjuvants such as tricine and quinic acid into the coordination complex yields products that—surprisingly and unexpectedly—exhibit both a therapeutically relevant solubility and a therapeutically acceptable pH, thus providing effective and safe I.V. formulations for SAHA.

As noted in the description above and as evidenced by the solubility data for compound 3 shown in Table 2, a complex of SAHA coordinated with a transition metal (viz., Ni) as opposed to an s-block metal (e.g., Mg or Ca) results in a complex that is even less soluble than SAHA itself—a reduction in solubility that, based on present understanding, is attributable to the fact that transition metals bind SAHA too tightly (i.e., confer too much covalency to the complex).

As shown in Table 2, the pH of a solution of Ca(saha)$_2$ (compound 2) is actually slightly higher than the pH of a solution of SAHA itself. However, this increase in pH is not to be automatically construed as reflecting a corresponding increase in pK$_a$. The distinction can be explained as follows and is worth bearing in mind when evaluating the data in Table 2. First, references to pK$_a$ refer to the pK$_a$ of a proton attached to a neutral or fully protonated biologically active agent or a metal-coordinated biologically active agent. However, in the case of a metal-coordinated biologically active agent such as Ca(saha)$_2$, the SAHA moiety is deprotonated relative to SAHA itself. The pH of the deprotonated salt of SAHA is around 10 as revealed by Na(saha). Therefore, the pH of a solution of Ca(saha)$_2$ does not necessarily reflect the pK$_a$ of the corresponding protonated species.

Anticancer Activity Testing: To test whether the incorporation of SAHA into a coordination complex affects its anticancer activity, cell proliferation assays were conducted. In the experiment, MDA-MB-231 breast cancer cells were plated (500 cells/well) on a 96-well plate and grown in culture for 24 hours. Drug solution was added and the cells were incubated for 48 hours. The drug medium was removed and the number of cells determined using the MTS method. As shown in FIG. 5, the data demonstrate that SAHA-containing coordination complexes inhibit breast cancer cell growth at concentrations (2.5-5 mM) for which SAHA is active.

The foregoing detailed description and accompanying figures have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. A metal coordination complex of a biologically active moiety and a metal, wherein the biologically active moiety is selected from the group consisting of: fingolimod, acamprosate, tixocortol, pregabalin, 7-phenyl-2,4,6-hepta-trienal hydroxamic acid, (S)-(+)-a-amino-4-carboxy-2-methylbenzeneacetic acid, eglumegad, (2S,2'R,3'R)-2-(2',3'-dicarboxycyclo-propyl)glycine, remacemide, zonisamide, balsalazide, dobutamine, ganciclovir, modafinil, ribavirin, zoledronic acid, and their derivatives.

2. A pharmaceutical composition comprising a pharmaceutically acceptable excipient and a metal coordination complex of a biologically active moiety and a metal, wherein the biologically active moiety is selected from the group consisting of: fingolimod, acamprosate, tixocortol, pregabalin, 7-phenyl-2,4,6-hepta-trienal hydroxamic acid, (S)-(+)-a-amino-4-carboxy-2-methylbenzeneacetic acid, eglumegad, (2S,2'R,3'R)-2-(2',3'-dicarboxycyclo-propyl)glycine, remacemide, zonisamide, balsalazide, dobutamine, ganciclovir, modafinil, ribavirin, zoledronic acid, and their derivatives.

3. The composition of claim 2, wherein the metal is selected from: s-block metals, d-block metals, and p-block metals.

4. The composition of claim 2, wherein the biologically active moiety is fingolimod.

5. The composition of claim 2, wherein the biologically active moiety is acamprosate.

6. The composition of claim 2, wherein the biologically active moiety is tixocortol.

7. The composition of claim 2, wherein the biologically active moiety is pregabalin.

8. The composition of claim 2, wherein the biologically active moiety is 7-phenyl-2,4,6-hepta-trienal hydroxamic acid.

9. The composition of claim 2, wherein the biologically active moiety is (S)-(+)-a-amino-4-carboxy-2-methylbenzeneacetic acid.

10. The composition of claim 2, wherein the biologically active moiety is eglumegad.

11. The composition of claim 2, wherein the biologically active moiety is (2S,2'R,3'R)-2-(2',3'-dicarboxycyclo-propyl)glycine.

12. The composition of claim 2, wherein the biologically active moiety is remacemide.

13. The composition of claim 2, wherein the biologically active moiety is zonisamide.

14. The composition of claim 2, wherein the biologically active moiety is balsalazide.

15. The composition of claim 2, wherein the biologically active moiety is dobutamine.

16. The composition of claim 2, wherein the biologically active moiety is ganciclovir.

17. The composition of claim 2, wherein the biologically active moiety is modafinil.

18. The composition of claim 2, wherein the biologically active moiety is ribavirin.

19. The composition of claim 2, wherein the biologically active moiety is zoledronic acid.

20. The pharmaceutical composition of claim 2, wherein the biologically active moiety is selected from the group consisting of: fingolimod, acamprosate, tixocortol, pregabalin, 7-phenyl-2,4,6-hepta-trienal hydroxamic acid, (S)-(+)-a-amino-4-carboxy-2-methylbenzeneacetic acid, eglumegad, (2S,2'R,3'R)-2-(2',3'-dicarboxycyclo-propyl)glycine, remacemide, zonisamide, balsalazide, dobutamine, ganciclovir, modafinil, ribavirin, and zoledronic acid.

21. The complex of claim 20, wherein the metal is selected from: s-block metals, d-block metals, and p-block metals.

* * * * *